United States Patent
Wang et al.

(10) Patent No.: US 9,890,155 B2
(45) Date of Patent: Feb. 13, 2018

(54) AZA-OXO-INDOLES FOR THE TREATMENT AND PROPHYLAXIS OF RESPIRATORY SYNCYTIAL VIRUS INFECTION

(71) Applicant: Hoffmann-La Roche Inc., Little Falls, NJ (US)

(72) Inventors: Lisha Wang, Basel (CH); Hongying Yun, Shanghai (CN); Weixing Zhang, Shanghai (CN); Xiufang Zheng, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/041,950

(22) Filed: Feb. 11, 2016

(65) Prior Publication Data
US 2016/0159794 A1    Jun. 9, 2016

Related U.S. Application Data

(63) Continuation of application No. PCT/EP2014/067197, filed on Aug. 12, 2014.

(30) Foreign Application Priority Data

Aug. 15, 2013 (WO) ................ PCT/CN2013/081563

(51) Int. Cl.
C07D 403/06 (2006.01)
C07D 471/04 (2006.01)
C07D 401/06 (2006.01)

(52) U.S. Cl.
CPC ......... *C07D 471/04* (2013.01); *C07D 401/06* (2013.01); *C07D 403/06* (2013.01)

(58) Field of Classification Search
CPC ... C07D 471/04; C07D 401/06; C07D 403/06
USPC ....................................................... 546/113
See application file for complete search history.

(56) References Cited

U.S. PATENT DOCUMENTS

| | | | | |
|---|---|---|---|---|
| 2002/0099208 A1* | 7/2002 | Yu | .................. | C07D 209/02 544/60 |
| 2016/0068531 A1* | 3/2016 | Wang | .................. | C07D 471/04 514/228.2 |
| 2016/0229853 A1* | 8/2016 | Gao | .................. | C07D 471/04 |
| 2016/0318943 A1* | 11/2016 | He | .................. | C07D 403/06 |

FOREIGN PATENT DOCUMENTS

| WO | 2012/080446 A1 | 6/2012 |
|---|---|---|
| WO | WO 2013068769 * | 5/2013 |
| WO | WO 2014060411 * | 4/2014 |
| WO | WO 2014184163 * | 11/2014 |
| WO | WO 2015022263 * | 2/2015 |
| WO | WO 2015158653 * | 10/2015 |

OTHER PUBLICATIONS

Combrink, Bioorganic & Medicinal Chemistry Letters (2007), 17(17), 4784-4790.*
Meanwell; Antiviral Drugs (2011), 353-366.*
Pryde; Bioorganic & Medicinal Chemistry Letters 23 (2013) 827-833.*
(Author Not Identified) Ansel's Pharmaceutical Dosage Forms and Drug Delivery Systems (Table of Contents only, in 6 pages), Allen et al., 8th edition, Philadelphia, PA: Lippincott Williams & Wilkins (2004).
(Author Not Identified) Handbook of Pharmaceutical Excipients (Cover and Table of Contents, total in 6 pages), Rowe et al., 5th edition, Grayslake, IL: Pharmaceutical Press (2005).
(Author Not Identified) Remington: The Science and Practice of Pharmacy (Cover and Table of Contents only, total in 4 pages), Gennaro et al., 20th edition, Philadelphia, PA: Lippincott Williams & Wilkins, (2000).
Ansel et al., Pharmaceutical Dosage Forms and Drug Delivery Systems Balado et al., Sixth edition, Malvern, PA:Williams & Wilkins, Table of Contents & pp. 196-197 (total in 6 pages) (1995).
Bastin et al., "Salt selection and optimisation procedures for pharmaceutical new chemical entities", Organic Process Res & Dev, 4:427-435 (2000).
DeVincenzo et al., "A randomized, double-blind, placebo-controlled study of an RNAi-based therapy directed against respiratory syncytial virus", PNAS, 107(19):8800-8805 (May 11, 2010).
Feltes et al., "A Randomized Controlled Trial of Motavizumab Versus Palivizumab for the Prophylaxis of Serious Respiratory Syncytial Virus Disease in Children With Hemodynamically Significant Congenital Heart Disease", Pediatric Research, 70(2):186-191 (2011).
Feltes et al., "Palivizumab prophylaxis reduces hospitalization due to respiratory syncytial viurs in young children with hemodynamically significant congenital heart disease", The Journal of Pediatrics, 143(4):532-540 (Oct. 2003).
International Preliminary Report on Patentability issued in International Application No. PCT/EP2014/067197, dated Feb. 16, 2016 (in 8 pages).

(Continued)

*Primary Examiner* — Daniel Carcanague
(74) *Attorney, Agent, or Firm* — Kevin M. Clark

(57) ABSTRACT

The invention provides novel compounds having the general formula:

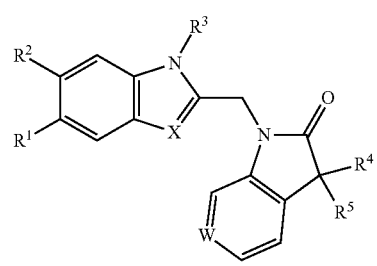

wherein $R^1$, $R^2$, $R^3$, $R^4$, $R^5$, W and X are as described herein, compositions including the compounds and methods of using the compounds.

8 Claims, No Drawings

(56) References Cited

OTHER PUBLICATIONS

International Search Report issued in International Application No. PCT/EP2014/067197, dated Sep. 11, 2014 (in 4 pages).
The IMpact-RSV Study Group (no authors listed), "Palivizumab, a Humanized Respiratory Syncytial Virus Monoclonal Antibody, Reduces Hospitalization From Respiratory Syncytial Virus Infection in High-risk Infants", Pediatrics, 102(3):531-537 (Sep. 1998).
Written Opinion of International Searching Authority issued in International Application No. PCT/EP2014/067197, dated Sep. 11, 2014 (in 7 pages).
Yu et al., "Respiratory syncytial virus fusion inhibitors. Part 4: Optimization for oral bioavailability", Biorganic & Medicinal Chemistry Letters, 17(4):895-901 (Feb. 1, 2007).
Yu et al., "Respiratory syncytial virus inhibitors. Part 2: Benzimidazol-2-one derivatives", Bioorganic & Medicinal Chemistry Letters, 14(5):1133-1137 (Jan. 1, 2004).
Zamora et al., "RNA Interference Therapy in Lung Transplant Patients Infected with Respiratory Syncytial Virus", Am J Resp Crit Care, 183:531-538 (2011).

* cited by examiner

AZA-OXO-INDOLES FOR THE TREATMENT AND PROPHYLAXIS OF RESPIRATORY SYNCYTIAL VIRUS INFECTION

CROSS REFERENCE TO RELATED APPLICATIONS

This application is a continuation of International Application No. PCT/EP2014/067197 having an international filing date of Aug. 12, 2014, the entire content of which is hereby incorporated herein by reference, and which claims the benefits of PCT/CN2013/081563 having a filing date of Aug. 15, 2013.

The present invention relates to organic compounds useful for therapy and/or prophylaxis in a mammal, and in particular to respiratory syncytial virus (RSV) inhibitors useful for treating RSV infection.

FIELD OF THE INVENTION

Respiratory Syncytial Virus (RSV) belongs to the family of Paramyxoviridae, subfamily of Pneumovirinae. The human RSV is a major cause of acute upper and lower respiratory tract infection in infants and children. Almost all children are infected by RSV at least once by age of three. Natural human immunity against RSV is incomplete. In normal adults and elder children, RSV infection is mainly associated with upper respiratory track symptoms. Severe case of RSV infection often leads to bronchiolitis and pneumonia, which requires hospitalization. High-risk factors for lower respiratory tract infections include premature birth, congenital heart disease, chronic pulmonary disease, and immunocompromised conditions. A severe infection at young age may lead to recurrent wheezing and asthma. For the elderly, RSV-related mortality rate becomes higher with advancing age.

RSV Fusion (F) protein is a surface glycoprotein on the viral envelope which, together with the G surface glycoprotein, mediates viral entry into host cell. The F protein initiates viral penetration by fusing viral and host cellular membranes and subsequently promotes viral spread after infection by melding infected cells to adjacent uninfected cells, resulting in characteristic syncytial formation. By inhibiting viral entry and spread, it is expected that treatment with chemicals described here will decrease the duration and severity of respiratory symptoms and subsequent risk of prolonged hospitalization and complications. It is also expected to limit the ability of individuals to transmit RSV within households, nursing homes and the hospital setting to other hosts potentially at high risk of complications.

There is no RSV vaccine available for human use, despite of many attempts in subunit vaccine and live-attenuated vaccine approaches. Virazole®, the aerosol form of ribavirin, is the only approved antiviral drug for treatment of RSV infection. However, it is rarely used clinically, due to limited efficacy and potential side effects. Two marketed prophylaxis antibodies were developed by MedImmune (CA, USA).

RSV-IGIV (brand name RespiGam) is polyclonal-concentrated RSV neutralizing antibody administered through monthly infusion of 750 mg/kg in hospital (Wandstrat T L, Ann Pharmacother. 1997 January; 31(1):83-8). Subsequently, the usage of RSV-IGIV was largely replaced by palivizumab (brand name Synagis®), a humanized monoclonal antibody against RSV fusion (F) protein approved for prophylaxis in high-risk infants in 1998. When administered intramuscularly at 15 mg/kg once a month for the duration of RSV season, palivizumab demonstrated 45-55% reduction of hospitalization rate caused by RSV infection in selected infants (Pediatrics. 1998 September; 102(3):531-7; Feltes T F et al, J Pediatr. 2003 October; 143(4):532-40). Unfortunately, palivizumab is not effective in the treatment of established RSV infection. A newer version monoclonal antibody, motavizumab, was designed as potential replacement of palivizumab but failed to show additional benefit over palivizumab in recent Phase III clinical trials (Feltes T F et al, Pediatr Res. 2011 August; 70(2):186-91).

A number of small molecule RSV inhibitors have been discovered. Among them, only a few reached Phase I or II clinical trials. Arrow Therapeutics (now a group in AstraZeneca, UK) completed a five-year Phase II trial of nucleocapsid (N) protein inhibitor, RSV-604, in stem cell transplantation patients by February 2010 (www.clinicaltrials.gov), but has not released the final results. Most of other small molecules were put on hold for various reasons.

RNAi therapeutics against RSV has also been thoroughly studied. ALN-RSV01 (Alnylam Pharmaceuticals, MA, USA) is a siRNA targeting on RSV gene. A nasal spray administered for two days before and for three days after RSV inoculation decreased infection rate among adult volunteers (DeVincenzo J. et al, Proc Natl Acad Sci USA. 2010 May 11; 107(19):8800-5). In another Phase II trial using naturally infected lung transplantation patients, results were not sufficient for conclusion of antiviral efficacy, though certain health benefits have been observed (Zamora M R et al, Am J Respir Crit Care Med. 2011 Feb. 15; 183(4):531-8). Additional Phase IIb clinical trials in similar patient population for ALN-RSV01 are on-going (www.clinicaltrials.gov).

Nevertheless, safe and effective treatment for RSV disease is needed urgently.

SUMMARY OF THE INVENTION

Objects of the present invention are novel compounds of formula I, their manufacture, medicaments based on a compound in accordance with the invention and their production as well as the use of compounds of formula I for the treatment or prophylaxis of RSV infection.

DETAILED DESCRIPTION OF THE INVENTION

Definitions

As used herein, the term "$C_{1-6}$alkyl" alone or in combination signifies a saturated, linear- or branched chain alkyl group containing 1 to 6, particularly 1 to 4 carbon atoms, for example methyl, ethyl, propyl, isopropyl, 1-butyl, 2-butyl, tert-butyl and the like. Particular "$C_{1-6}$alkyl" groups are methyl, ethyl, isopropyl and tert-butyl.

The term "—$C_yH_{2y}$—" alone or in combination signifies a chemical link or a saturated, linear or branched chain alkyl group containing from 1 to 6 carbon atoms, particularly, the term signifies a chemical link or a saturated, linear or branched chain alkyl group containing from 1 to 4 carbon atoms.

The term "cycloalkyl", alone or in combination, refers to a saturated carbon ring containing from 3 to 7 carbon atoms, particularly from 3 to 6 carbon atoms, for example, cyclopropyl, cyclobutyl, cyclopentyl, cyclohexyl, cycloheptyl and the like. Particular "cycloalkyl" groups are cyclopropyl, cyclopentyl and cyclohexyl.

The term "$C_{1-6}$alkoxy" alone or in combination signifies a group $C_{1-6}$alkyl-O—, wherein the "$C_{1-6}$alkyl" is as defined above; for example methoxy, ethoxy, propoxy, iso-propoxy, n-butoxy, iso-butoxy, 2-butoxy, tert-butoxy and the like. Particular "$C_{1-6}$alkoxy" groups are methoxy and ethoxy and more particularly methoxy.

The term "cyano" alone or in combination refers to the group —CN.

The term "amino", alone or in combination, refers to primary (—NH$_2$), secondary (—NH—) or tertiary amino $$(-N\diagup\diagdown\ ).$$

The term "halogen" means fluorine, chlorine, bromine or iodine. Halogen is particularly fluorine, chlorine or bromine.

The term "hydroxy" alone or in combination refers to the group —OH.

The term "carbonyl" alone or in combination refers to the group —C(O)—.

The term "carboxy" alone or in combination refers to the group —COOH.

The term "sulfonyl" alone or in combination refers to the group —S(O)$_2$—.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin R. J., et al., Organic Process Research & Development 2000, 4, 427-435; or in Ansel, H., et al., In: Pharmaceutical Dosage Forms and Drug Delivery Systems, 6th ed. (1995), pp. 196 and 1456-1457. Particular are the sodium salts of the compounds of formula I.

Compounds of the general formula I which contain one or several chiral centers can either be present as racemates, diastereomeric mixtures, or optically active single isomers. The racemates can be separated according to known methods into the enantiomers. Particularly, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

Inhibitors of RSV Fusion Protein

The present invention provides (i) novel compounds having the general formula I:

(I)

wherein
W is nitrogen or —CR$^9$, wherein R$^9$ is halogen;
X is nitrogen or —CR$^{10}$, provided that
when X is —CR$^{10}$, R$^1$ is hydrogen, R$^2$ is halogen, R$^3$ is hydrogen, wherein R$^{10}$ is $C_{1-6}$alkylsulfonylphenyl;
when X is nitrogen, R$^1$ is halogen, R$^2$ is hydrogen, R$^3$ is R$^4$ and R$^5$, with the carbon atom to which they are attached, form cycloalkyl;
R$^6$ is hydrogen or $C_{1-6}$alkyl;
R$^7$ is hydrogen, aminocarbonyl, $C_{1-6}$alkoxycarbonyl-$C_yH_{2y}$—, $C_{1-6}$ alkylcarbonyl, $C_{1-6}$alkylsulfonyl, carboxy or cyano, wherein y is 0-6;
R$^8$ is $C_{1-6}$alkylsulfonyl, $C_{1-6}$alkoxy, cyano or hydroxy;
or pharmaceutically acceptable salts thereof.

Further embodiment of present invention is (ii) a compound of formula I, wherein
W is nitrogen or —CF;
X is nitrogen or —CR$^{10}$, provided that
when X is —CR$^{10}$, R$^1$ is hydrogen, R$^2$ is chloro, R$^3$ is hydrogen, wherein R$^{10}$ is methylsulfonylphenyl;
when X is nitrogen, R$^1$ is chloro, R$^2$ is hydrogen, R$^3$ is R$^4$ and R$^5$, with the carbon atom to which they are attached, form cyclopropyl;
R$^6$ is hydrogen or methyl;
R$^7$ is hydrogen, aminocarbonyl, ethoxycarbonyl, methoxycarbonyl, ethoxycarbonylmethyl, methylcarbonyl, methyl sulfonyl, carboxy or cyano;
R$^8$ is methoxy, methylsulfonyl, ethylsulfonyl, cyano or hydroxy;
or pharmaceutically acceptable salts thereof.

Another embodiment of present invention is (iii) a compound of formula I or a pharmaceutically acceptable salt thereof, wherein
R$^1$ is halogen;
R$^2$ is hydrogen;

$R^3$ is

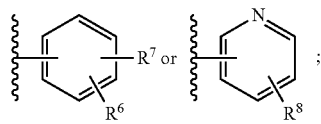

$R^4$ and $R^5$, with the carbon atom to which they are attached, form cycloalkyl;
$R^6$ is hydrogen or $C_{1-6}$alkyl;
$R^7$ is hydrogen, aminocarbonyl, $C_{1-6}$alkoxycarbonyl-$C_yH_{2y}$—, $C_{1-6}$ alkylcarbonyl, $C_{1-6}$alkylsulfonyl, carboxy or cyano, wherein y is 0-6;
$R^8$ is $C_{1-6}$alkylsulfonyl, $C_{1-6}$alkoxy, cyano or hydroxy;
W is nitrogen;
X is nitrogen.

Further embodiment of present invention is (iv) a compound of formula I or a pharmaceutically acceptable salt thereof, wherein
$R^1$ is chloro;
$R^2$ is hydrogen;
$R^3$ is

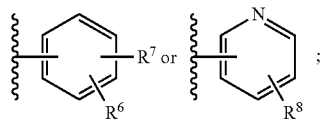

$R^4$ and $R^5$, with the carbon atom to which they are attached, form cyclopropyl;
$R^6$ is hydrogen or methyl;
$R^7$ is hydrogen, aminocarbonyl, ethoxycarbonyl, methoxycarbonyl, ethoxycarbonylmethyl, methylcarbonyl, methyl sulfonyl, carboxy or cyano;
$R^8$ is methoxy, methylsulfonyl, ethylsulfonyl, cyano or hydroxy;
W is nitrogen;
X is nitrogen.

Another embodiment of present invention is (v) a compound of formula I or a pharmaceutically acceptable salt thereof, wherein
$R^1$ is hydrogen;
$R^2$ is halogen;
$R^3$ is hydrogen;
$R^4$ and $R^5$, with the carbon atom to which they are attached, form cycloalkyl;
W is nitrogen;
X is —$CR^{10}$, wherein $R^{10}$ is $C_{1-6}$alkylsulfonylphenyl.

Another embodiment of present invention is (vi) a compound of formula I or a pharmaceutically acceptable salt thereof, wherein
$R^1$ is halogen;
$R^2$ is hydrogen;
$R^3$ is carboxyphenyl;
$R^4$ and $R^5$, with the carbon atom to which they are attached, form cycloalkyl;
W is —$CR^9$, wherein $R^9$ is halogen;
X is nitrogen.

Particular compounds of formula I, including their activity data, NMR data and MS data are summarized in the following Table 1 and 2.

TABLE 1

Structure, name and activity data of particular compounds

| Example No. | Structure | Name | CPE Long $EC_{50}$ (μM) |
|---|---|---|---|
| 1 | 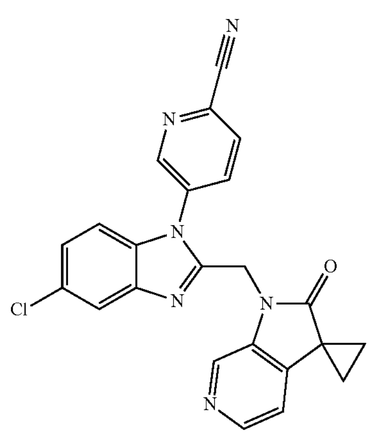 [SMILES: N#Cc1ccc(-n2c(CN3C(=O)C4(CC4)c4ccncc43)nc3cc(Cl)ccc32)cn1] | 5-{5-Chloro-2-[(2'-oxospiro[cyclopropane-1,3'-pyrrolo[2,3-c]pyridin]-1'(2'H)-yl)methyl]-1H-benzimidazol-1-yl}pyridine-2-carbonitrile | 0.0007 |

TABLE 1-continued

Structure, name and activity data of particular compounds

| Example No. | Structure | Name | CPE Long $EC_{50}$ (μM) |
|---|---|---|---|
| 2-1 | 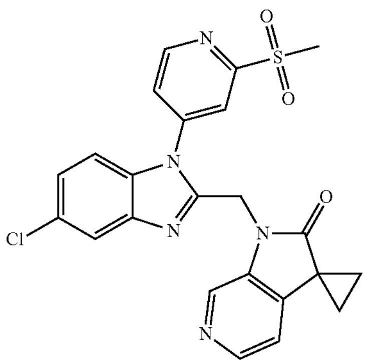 | 1'-({5-Chloro-1-[2-(methylsulfonyl)pyridin-4-yl]-1H-benzimidazol-2-yl}methyl)spiro[cyclopropane-1,3'-pyrrolo[2,3-c]pyridin]-2'(1'H)-one | 0.065 |
| 2-2 | 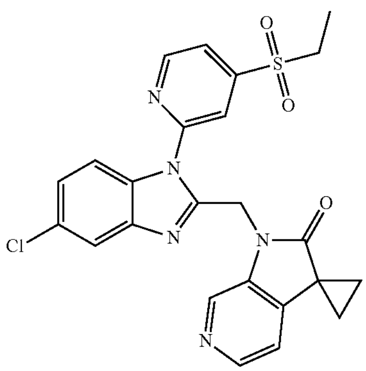 [SMILES: CCS(=O)(=O)c1ccnc(-n2c(CN3C(=O)C4(CC4)c4ccncc43)nc3cc(Cl)ccc32)c1] | 1'-({5-Chloro-1-[4-(ethylsulfonyl)pyridin-2-yl]-1H-benzimidazol-2-yl}methyl)spiro[cyclopropane-1,3'-pyrrolo[2,3-c]pyridin]-2'(1'H)-one | 0.021 |
| 3 | 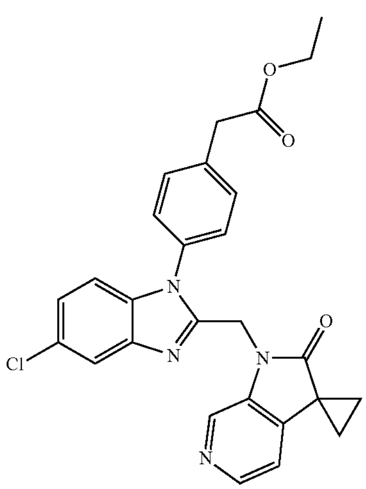 [SMILES: CCOC(=O)Cc1ccc(-n2c(CN3C(=O)C4(CC4)c4ccncc43)nc3cc(Cl)ccc32)cc1] | Ethyl (4-{5-chloro-2-[(2'-oxospiro[cyclopropane-1,3'-pyrrolo[2,3-c]pyridin]-1'(2'H)-yl)methyl]-1H-benzimidazol-1-yl}phenyl)acetate | 0.014 |

TABLE 1-continued

Structure, name and activity data of particular compounds

| Example No. | Structure | Name | CPE Long EC$_{50}$ (μM) |
|---|---|---|---|
| 4-1 | 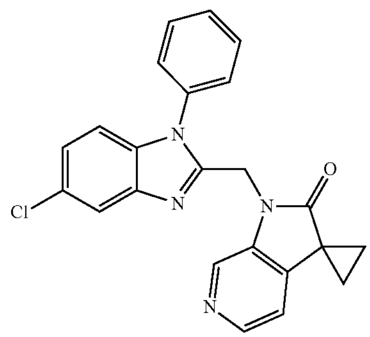 [SMILES: O=C1N(Cc2nc3cc(Cl)ccc3n2-c2ccccc2)c2cnccc2C12CC2] | 1'-[(5-Chloro-1-phenyl-1H-benzimidazol-2-yl)methyl]spiro[cyclopropane-1,3'-pyrrolo[2,3-c]pyridin]-2'(1'H)-one | 0.017 |
| 4-2 | 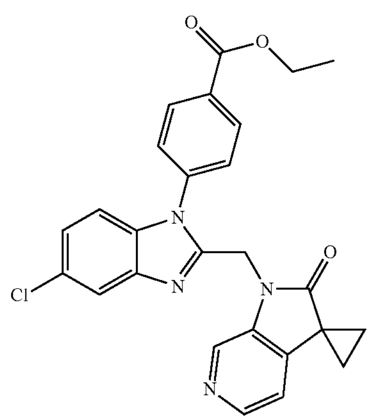 [SMILES: CCOC(=O)c1ccc(-n2c(CN3C(=O)C4(CC4)c4ccncc43)nc3cc(Cl)ccc32)cc1] | Ethyl 4-{5-chloro-2-[(2'-oxospiro[cyclopropane-1,3'-pyrrolo[2,3-c]pyridin]-1'(2'H)-yl)methyl]-1H-benzimidazol-1-yl}benzoate | 0.006 |
| 4-3 | 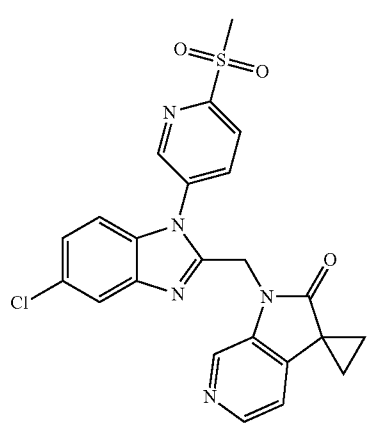 [SMILES: CS(=O)(=O)c1ccc(-n2c(CN3C(=O)C4(CC4)c4ccncc43)nc3cc(Cl)ccc32)cn1] | 1'-({5-Chloro-1-[6-(methylsulfonyl)pyridin-3-yl]-1H-benzimidazol-2-yl}methyl)spiro[cyclopropane-1,3'-pyrrolo[2,3-c]pyridin]-2'(1'H)-one | 0.004 |

TABLE 1-continued

Structure, name and activity data of particular compounds

| Example No. | Structure | Name | CPE Long EC$_{50}$ (μM) |
|---|---|---|---|
| 4-4 | 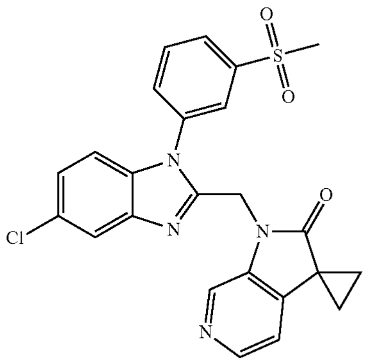 | 1'-({5-chloro-1-[3-(methylsulfonyl)phenyl]-1H-benzimidazol-2-yl}methyl)spiro[cyclopropane-1,3'-pyrrolo[2,3-c]pyridin]-2'(1'H)-one | 0.008 |
| 4-5 | 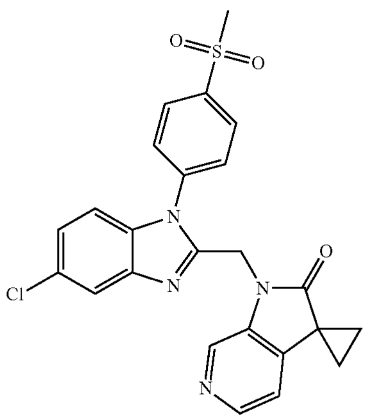 [SMILES: CS(=O)(=O)c1ccc(-n2c(CN3C(=O)C4(CC4)c4ccncc43)nc3cc(Cl)ccc32)cc1] | 1'-({5-chloro-1-[4-(methylsulfonyl)phenyl]-1H-benzimidazol-2-yl}methyl)spiro[cyclopropane-1,3'-pyrrolo[2,3-c]pyridin]-2'(1'H)-one | 0.005 |
| 4-6 | 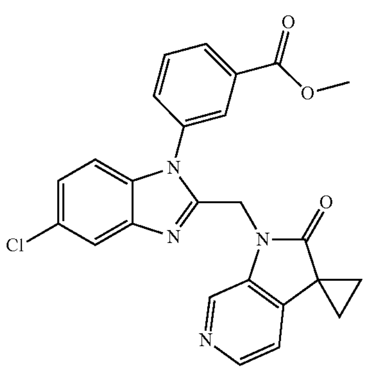 [SMILES: COC(=O)c1cccc(-n2c(CN3C(=O)C4(CC4)c4ccncc43)nc3cc(Cl)ccc32)c1] | Methyl 3-{5-chloro-2-[(2'-oxospiro[cyclopropane-1,3'-pyrrolo[2,3-c]pyridin]-1'(2'H)-yl)methyl]-1H-benzimidazol-1-yl}benzoate | 0.016 |
| 4-7 | 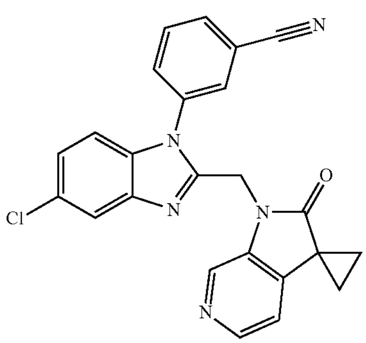 [SMILES: N#Cc1cccc(-n2c(CN3C(=O)C4(CC4)c4ccncc43)nc3cc(Cl)ccc32)c1] | 3-{5-Chloro-2-[(2'-oxospiro[cyclopropane-1,3'-pyrrolo[2,3-c]pyridin-1'(2'H)-yl)methyl]-1H-benzimidazol-1-yl}benzonitrile | 0.007 |

TABLE 1-continued

Structure, name and activity data of particular compounds

| Example No. | Structure | Name | CPE Long $EC_{50}$ (μM) |
|---|---|---|---|
| 4-8 | 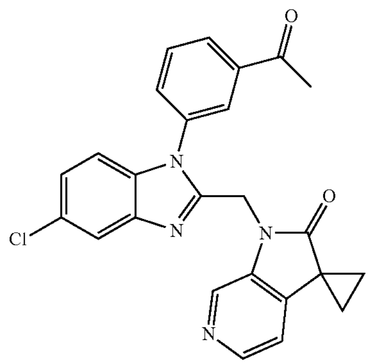 [SMILES: CC(=O)c1cccc(-n2c(CN3C(=O)C4(CC4)c4ccncc43)nc3cc(Cl)ccc32)c1] | 1'-{[1-(3-Acetylphenyl)-5-chloro-1H-benzimidazol-2-yl]methyl}spiro[cyclopropane-1,3'-pyrrolo[2,3-c]pyridin]-2'(1'H)-one | 0.019 |
| 4-9 | 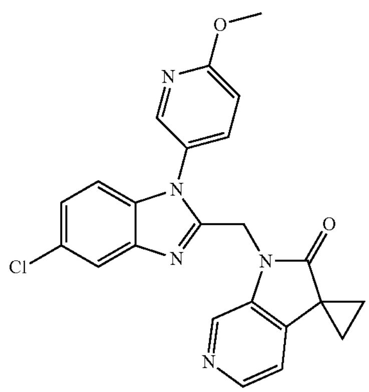 [SMILES: COc1ccc(-n2c(CN3C(=O)C4(CC4)c4ccncc43)nc3cc(Cl)ccc32)cn1] | 1'-{[5-Chloro-1-(6-methoxypyridin-3-yl)-1H-benzimidazol-2-yl]methyl}spiro[cyclopropane-1,3'-pyrrolo[2,3-c]pyridin]-2'(1'H)-one | 0.011 |
| 5-1 | 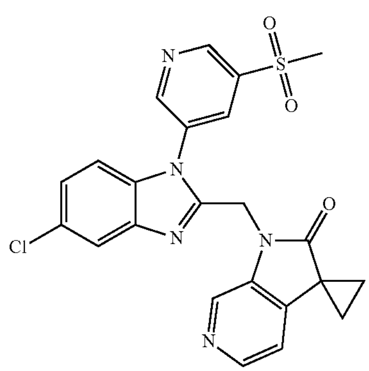 [SMILES: CS(=O)(=O)c1cncc(-n2c(CN3C(=O)C4(CC4)c4ccncc43)nc3cc(Cl)ccc32)c1] | 1'-({5-Chloro-1-[5-(methylsulfonyl)pyridin-3-yl]-1H-benzimidazol-2-yl}methyl)spiro[cyclopropane-1,3'-pyrrolo[2,3-c]pyridin]-2'(1'H)-one | 0.005 |
| 5-2 | 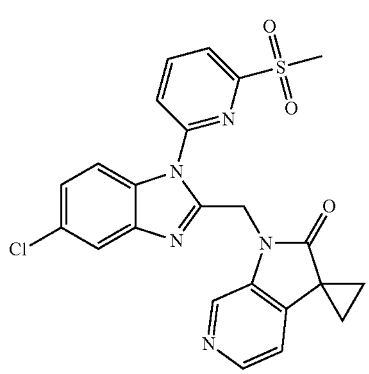 [SMILES: CS(=O)(=O)c1cccc(-n2c(CN3C(=O)C4(CC4)c4ccncc43)nc3cc(Cl)ccc32)n1] | 1'-({5-Chloro-1-[6-(methylsulfonyl)pyridin-2-yl]-1H-benzimidazol-2-yl}methyl)spiro[cyclopropane-1,3'-pyrrolo[2,3-c]pyridin]-2'(1'H)-one | 0.005 |

TABLE 1-continued

Structure, name and activity data of particular compounds

| Example No. | Structure | Name | CPE Long EC$_{50}$ (μM) |
|---|---|---|---|
| 5-3 | 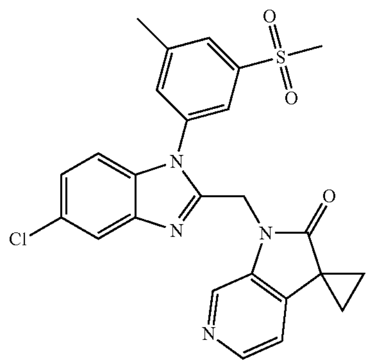 [SMILES: Cc1cc(-n2c(CN3C(=O)C4(CC4)c4ccncc43)nc3cc(Cl)ccc32)cc(S(C)(=O)=O)c1] | 1'-({5-Chloro-1-[3-methyl-5-(methylsulfonyl)phenyl]-1H-benzimidazol-2-yl}methyl)spiro[cyclopropane-1,3'-pyrrolo[2,3-c]pyridin]-2'(1'H)-one | 0.019 |
| 6-1 | 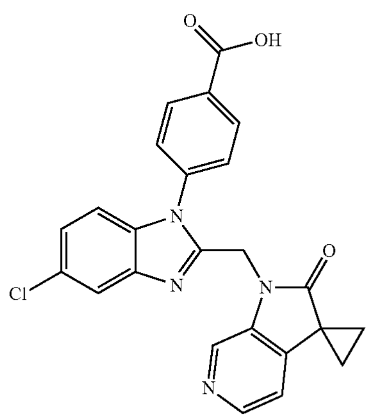 [SMILES: O=C(O)c1ccc(-n2c(CN3C(=O)C4(CC4)c4ccncc43)nc3cc(Cl)ccc32)cc1] | 4-{5-Chloro-2-[(2'-oxospiro[cyclopropane-1,3'-pyrrolo[2,3-c]pyridin]-1'(2'H)-yl)methyl]-1H-benzimidazol-1-yl}benzoic acid | 0.006 |
| 6-2 | 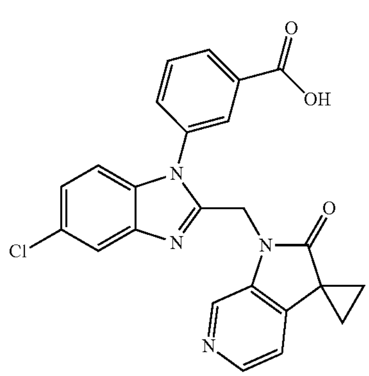 [SMILES: O=C(O)c1cccc(-n2c(CN3C(=O)C4(CC4)c4ccncc43)nc3cc(Cl)ccc32)c1] | 3-{5-Chloro-2-[(2'-oxospiro[cyclopropane-1,3'-pyrrolo[2,3-c]pyridin]-1'(2'H)-yl)methyl]-1H-benzimidazol-1-yl}benzoic acid | 0.512 |

TABLE 1-continued

Structure, name and activity data of particular compounds

| Example No. | Structure | Name | CPE Long EC$_{50}$ (μM) |
|---|---|---|---|
| 6-3 | 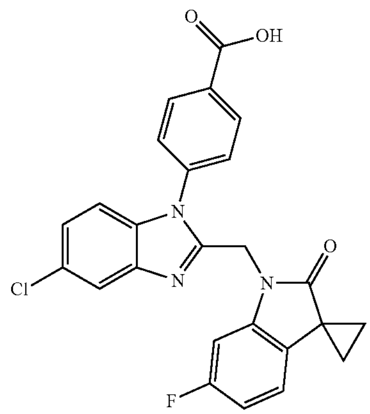 [SMILES: O=C(O)c1ccc(-n2c(CN3C(=O)C4(CC4)c4ccc(F)cc43)nc3cc(Cl)ccc32)cc1] | 4-{5-Chloro-2-[(6'-fluoro-2'-oxospiro[cyclopropane-1,3'-indol]-1'(2'H)-yl)methyl]-1H-benzimidazol-1-yl}benzoic acid | 0.05 |
| 7 | 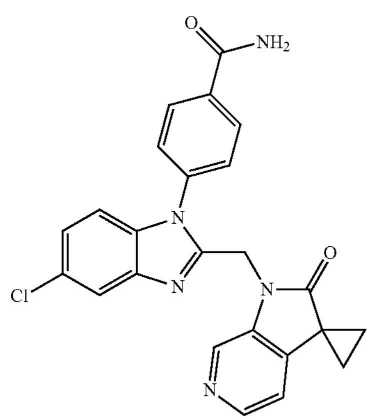 [SMILES: NC(=O)c1ccc(-n2c(CN3C(=O)C4(CC4)c4ccncc43)nc3cc(Cl)ccc32)cc1] | 4-{5-Chloro-2-[(6'-fluoro-2'-oxospiro[cyclopropane-1,3'-indol]-1'(2'H)-yl)methyl]-1H-benzimidazol-1-yl}benzoic acid | 0.013 |
| 8 | 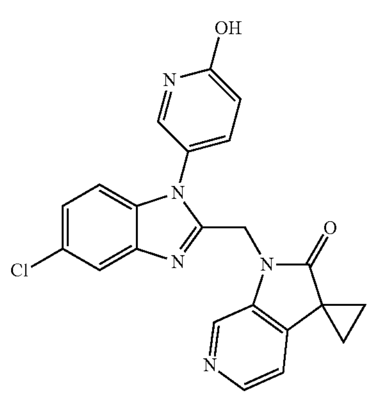 [SMILES: O=C1N(Cc2nc3cc(Cl)ccc3n2-c2ccc(O)nc2)c2cnccc2C12CC2] | 1'-{[5-Chloro-1-(6-hydroxypyridin-3-yl)-1H-benzimidazol-2-yl]methyl}spiro[cyclopropane-1,3'-pyrrolo[2,3-c]pyridin]-2'(1'H)-one | 0.018 |

TABLE 1-continued

Structure, name and activity data of particular compounds

| Example No. | Structure | Name | CPE Long EC$_{50}$ (μM) |
|---|---|---|---|
| 9-1 | 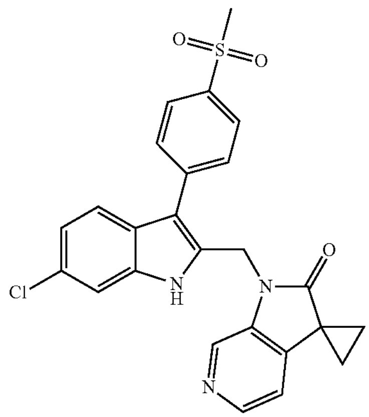 [SMILES: CS(=O)(=O)c1ccc(-c2c(CN3C(=O)C4(CC4)c4ccncc43)[nH]c3cc(Cl)ccc23)cc1] | 1'-({6-Chloro-3-[4-(methylsulfonyl)phenyl]-1H-indol-2-yl}methyl)spiro[cyclopropane-1,3'-pyrrolo[2,3-c]pyridin]-2'(1'H)-one | 0.025 |
| 9-2 | 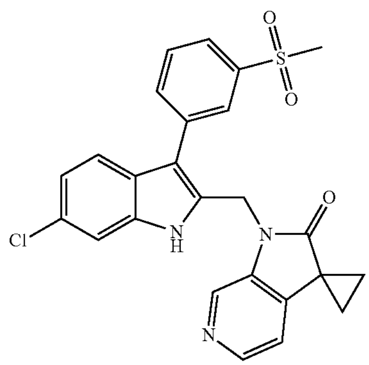 [SMILES: CS(=O)(=O)c1cccc(-c2c(CN3C(=O)C4(CC4)c4ccncc43)[nH]c3cc(Cl)ccc23)c1] | 1'-({6-Chloro-3-[3-(methylsulfonyl)phenyl]-1H-indol-2-yl}methyl)spiro[cyclopropane-1,3'-pyrrolo[2,3-c]pyridin]-2'(1'H)-one | 0.029 |

TABLE 2

NMR and MS data of particular compounds

| Example No. | $^1$H NMR data | MW data |
|---|---|---|
| 1 | $^1$H NMR (400 MHz, CDCl$_3$) δ ppm 8.42 (s, 1 H), 8.41 (s, 1 H), 8.28 (s, 1 H), 7.89-7.81 (m, 3 H), 7.29-7.26 (m, 2 H), 6.93-6.91 (d, J = 8.8 Hz, 1 H), 6.77-6.76 (m, 1 H), 5.31 (s, 2 H), 1.65-1.62 (m, 2 H), 1.59-1.56 (m, 2 H) | MS obsd. (ESI$^+$) [(M + H)$^+$] 427 |
| 2-1 | $^1$H NMR (400 MHz, CD$_3$OD) δ ppm 8.93 (d, J = 5.05 Hz, 1 H), 8.21 (d, J = 4.80 Hz, 1 H), 8.19-8.14 (m, 1 H), 8.12 (s, 1 H), 7.81-7.75 (m, 2 H), 7.35 (dd, J = 8.72, 1.64 Hz, 1 H), 7.26 (d, J = 8.84 Hz, 1 H), 7.05 (d, J = 4.80 Hz, 1 H), 5.45 (s, 2 H), 3.35 (br. s., 3 H), 1.77-1.69 (m, 2 H), 1.63-1.56 (m, 2 H) | MS obsd. (ESI$^+$) [(M + H)$^+$] 480 |
| 2-2 | $^1$H NMR (400 MHz, CD$_3$OD) δ ppm 8.97 (d, J = 5.05 Hz, 1 H), 8.27-8.18 (m, 2 H), 8.17 (s, 1 H), 8.05 (dd, J = 5.05, 1.26 Hz, 1 H), 7.74 (d, J = 1.52 Hz, 1 H), 7.46 (d, J = 8.84 Hz, 1 H), 7.39 (dd, J = 8.72, 1.89 Hz, 1 H), 7.11 (d, J = 4.55 Hz, 1 H), 5.56 (s, 2 H), 3.46 (q, J = 7.30 Hz, 2 H), 1.84-1.77 (m, 2 H), 1.75-1.68 (m, 2 H), 1.37 (t, J = 7.33 Hz, 3 H) | MS obsd. (ESI$^+$) [(M + H)$^+$] 494 |
| 3 | $^1$H NMR (400 MHz, DMSO-d$_6$) δ ppm 8.22 (s, 1 H), 8.14 (s, 1 H), 8.80 (d, J = 2.0 Hz, 1 H), 7.48 (s, 4 H), 7.27 (dd, J = 4.4, 13.2 Hz, 1 H), 7.14 (s, 1 H), 7.12 (m, 2 H), 5.26 (d, J = 4.0 Hz, 2 H), 4.14 (q, J = 7.2 Hz, 2 H), 3.80 (s, 2 H), 1.74 (m, 2 H), 1.54 (m, 2 H), 1.24 (t, J = 7.2 Hz, 3 H) | MS obsd. (ESI$^+$) [(M + H)$^+$] 487 |
| 4-1 | $^1$H NMR (400 MHz, CD$_3$OD) δ ppm 8.21 (d, J = 5.05 Hz, 1 H), 8.03 (s, 1 H), 7.69 (d, J = 1.52 Hz, 1 H), 7.61-7.49 (m, 3 H), 7.42-7.32 (m, 2 H), 7.26 (dd, J = 8.59, 1.77 Hz, 1 H), 7.11-7.01 (m, 2 H), 5.34 (s, 2 H), 1.77-1.70 (m, 2 H), 1.68-1.58 (m, 2 H) | MS obsd. (ESI$^+$) [(M + H)$^+$] 401 |

TABLE 2-continued

NMR and MS data of particular compounds

| Example No. | $^1$H NMR data | MW data |
|---|---|---|
| 4-2 | $^1$H NMR (400 MHz, CD$_3$OD) δ ppm 8.22 (d, J = 5.05 Hz, 1 H), 8.17 (d, J = 8.59 Hz, 2 H), 8.04 (s, 1 H), 7.75 (d, J = 1.77 Hz, 1 H), 7.50 (d, J = 8.59 Hz, 2 H), 7.32 (dd, J = 8.72, 1.89 Hz, 1 H), 7.16 (d, J = 8.84 Hz, 1 H), 7.07 (d, J = 4.80 Hz, 1 H), 5.41 (s, 2 H), 4.46 (q, J = 7.24 Hz, 2 H), 1.75-1.69 (m, 2 H), 1.63-1.58 (m, 2 H), 1.45 (t, J = 7.07 Hz, 3 H) | MS obsd. (ESI$^+$) [(M + H)$^+$] 473 |
| 4-3 | $^1$H NMR (400 MHz, CD$_3$OD) δ ppm 8.83 (s, 1 H), 8.28-8.21 (m, 3 H), 8.20 (s, 1 H), 7.78 (d, J = 1.52 Hz, 1 H), 7.34 (dd, J = 8.59, 1.77 Hz, 1 H), 7.21 (d, J = 8.84 Hz, 1 H), 7.08 (d, J = 4.80 Hz, 1 H), 5.42 (s, 2 H), 1.81-1.72 (m, 2 H), 1.70-1.61 (m, 2 H) | MS obsd. (ESI$^+$) [(M + H)$^+$] 480 |
| 4-4 | $^1$H NMR (400 MHz, CD$_3$OD) δ ppm 8.24-8.21 (m, 1 H), 8.18-8.13 (m, 1 H), 8.10-8.07 (m, 1 H), 8.04-7.99 (m, 1 H), 7.84-7.81 (m, 1 H), 7.80-7.77 (m, 1 H), 7.67-7.62 (m, 1 H), 7.35-7.30 (m, 1 H), 7.16-7.11 (m, 1 H), 7.08-7.04 (m, 1 H), 5.46-5.38 (m, 2 H), 3.26 (s, 3 H), 1.76-1.69 (m, 2 H), 1.63-1.52 (m, 2 H) | MS obsd. (ESI$^+$) [(M + H)$^+$] 479 |
| 4-5 | $^1$H NMR (400 MHz, CD$_3$OD) δ ppm 8.26-8.20 (m, 1 H), 8.16-8.10 (m, 2 H), 8.10-8.05 (m, 1 H), 7.78-7.75 (m, 1 H), 7.70-7.64 (m, 2 H), 7.36-7.30 (m, 1 H), 7.21-7.15 (m, 1 H), 7.09-7.04 (m, 1 H), 5.43 (s, 2 H), 3.23 (s, 3 H), 1.79-1.71 (m, 2 H), 1.68-1.61 (m, 2 H) | MS obsd. (ESI$^+$) [(M + H)$^+$] 479 |
| 4-6 | $^1$H NMR (400 MHz, CD$_3$OD) δ ppm 8.61-8.44 (m, 2 H), 8.32-8.1 (m, 1 H), 8.15-8.05 (m, 1 H), 7.89-7.61 (m, 4 H), 7.39-7.31 (m, 1 H), 7.24-7.10 (m, 1 H), 5.43-5.34 (m, 2 H), 3.97 (s, 3 H), 2.18-2.06 (m, 2 H), 2.02-1.92 (m, 2 H) | MS obsd. (ESI$^+$) [(M + H)$^+$] 459 |
| 4-7 | $^1$H NMR (400 MHz, CD$_3$OD) δ ppm 8.27-8.21 (m, 1 H), 8.15-8.12 (m, 1 H), 7.96-7.91 (m, 1 H), 7.89-7.85 (m, 3 H), 7.78-7.69 (m, 1 H), 7.35-7.30 (m, 1 H), 7.15-7.07 (m, 2 H), 5.42-5.33 (m, 2 H), 1.81-1.62 (m, 4 H) | MS obsd. (ESI$^+$) [(M + H)$^+$] 426 |
| 4-8 | $^1$H NMR (400 MHz, CD$_3$OD) δ ppm 8.21 (d, J = 5.05 Hz, 1 H), 8.14 (d, J = 7.83 Hz, 1 H), 8.04 (s, 1 H), 7.96 (t, J = 1.64 Hz, 1 H), 7.76 (d, J = 1.52 Hz, 1 H), 7.71-7.63 (m, 1 H), 7.58-7.52 (m, 1 H), 7.31 (dd, J = 8.72, 1.89 Hz, 1 H), 7.11 (d, J = 8.84 Hz, 1 H), 7.04 (d, J = 4.80 Hz, 1 H), 5.41 (s, 2 H), 2.62 (s, 3 H), 1.72-1.52 (m, 4 H) | MS obsd. (ESI$^+$) [(M + H)$^+$] 443 |
| 4-9 | $^1$H NMR (400 MHz, CD$_3$OD) δ ppm 8.28-8.20 (m, 1 H), 8.19-8.10 (m, 2 H), 7.80-7.70 (m, 1 H), 7.69-7.59 (m, 1 H), 7.37-7.25 (m, 1 H), 7.17-7.06 (m, 2 H), 6.99-6.86 (m, 1 H), 5.36 (s, 2 H), 4.01 (s, 3 H), 1.84-1.61 (m, 4 H) | MS obsd. (ESI$^+$) [(M + H)$^+$] 432 |
| 5-1 | $^1$H NMR (400 MHz, CD$_3$OD) δ ppm 9.28 (d, J = 2.02 Hz, 1 H), 8.87 (d, J = 2.27 Hz, 1 H), 8.54 (t, J = 2.15 Hz, 1 H), 8.30-8.20 (m, 2 H), 7.81 (d, J = 1.77 Hz, 1 H), 7.35 (dd, J = 8.72, 1.89 Hz, 1 H), 7.20 (d, J = 8.59 Hz, 1 H), 7.08 (d, J = 4.80 Hz, 1 H), 5.41 (s, 2 H), 3.36 (s, 3 H), 1.80-1.70 (m, 2 H), 1.65-1.56 (m, 2 H) | MS obsd. (ESI$^+$) [(M + H)$^+$] 480 |
| 5-2 | $^1$H NMR (400 MHz, CD$_3$OD) δ ppm 8.45 (t, J = 1.00 Hz, 1 H), 8.30-8.22 (m, 2 H), 8.19 (s, 1 H), 8.03 (d, J = 7.83 Hz, 1 H), 7.73 (d, J = 1.77 Hz, 1 H), 7.54 (d, J = 8.59 Hz, 1 H), 7.39 (dd, J = 8.72, 1.89 Hz, 1 H), 7.12 (d, J = 4.80 Hz, 1 H), 5.60 (s, 2 H), 3.36 (s, 3 H), 1.85-1.78 (m, 2 H), 1.78-1.70 (m, 2 H) | MS obsd. (ESI$^+$) [(M + H)$^+$] 480 |
| 5-3 | $^1$H NMR (400 MHz, CD$_3$OD) δ ppm 8.22 (d, J = 4.80 Hz, 1 H), 8.03 (s, 1 H), 7.95 (s, 1 H), 7.78 (d, J = 1.77 Hz, 1 H), 7.73 (s, 1 H), 7.43 (s, 1 H), 7.32 (dd, J = 8.72, 1.89 Hz, 1 H), 7.13 (d, J = 8.59 Hz, 1 H), 7.06 (d, J = 5.05 Hz, 1 H), 5.43 (s, 2 H), 3.22 (s, 3 H), 2.48 (s, 3 H), 1.75-1.68 (m, 2 H), 1.60-1.53 (m, 2 H) | MS obsd. (ESI$^+$) [(M + H)$^+$] 493 |
| 6-1 | $^1$H NMR (400 MHz, CD$_3$OD) δ ppm 8.22 (d, J = 4.80 Hz, 1 H), 8.16 (d, J = 8.59 Hz, 2 H), 8.03 (s, 1 H), 7.75 (d, J = 1.77 Hz, 1 H), 7.46 (d, J = 8.34 Hz, 2 H), 7.32 (dd, J = 8.72, 1.89 Hz, 1 H), 7.16 (d, J = 8.59 Hz, 1 H), 7.07 (d, J = 4.80 Hz, 1 H), 5.41 (s, 2 H), 1.75-1.69 (m, 2 H), 1.65-1.58 (m, 2 H) | MS obsd. (ESI$^+$) [(M + H)$^+$] 445 |
| 6-2 | $^1$H NMR (400 MHz, CD$_3$OD) δ ppm 8.25-8.19 (m, 1 H), 8.16-8.09 (m, 1 H), 8.09-8.04 (m, 1 H), 7.82-7.77 (m, 1 H), 7.75-7.68 (m, 1 H), 7.63-7.53 (m, 1 H), 7.53-7.45 (m, 1 H), 7.34-7.25 (m, 1 H), 7.19-7.12 (m, 1 H), 7.10-7.02 (m, 1 H), 5.40-5.34 (m, 2 H), 1.77-1.62 (m, 2 H), 1.37-1.26 (m, 2 H) | MS obsd. (ESI$^+$) [(M + H)$^+$] 445 |
| 6-3 | $^1$H NMR (400 MHz, CD$_3$OD) δ ppm 8.12 (d, J = 8.59 Hz, 2 H), 7.78-7.70 (m, 1 H), 7.36 (d, J = 8.59 Hz, 2 H), 7.29 (s, 1 H), 7.13 (d, J = 0.51 Hz, 1 H), 6.92-6.85 (m, 1 H), 6.78-6.69 (m, 1 H), 6.67-6.57 (m, 1 H), 5.33 (s, 2 H), 1.50 (s, 2 H), 1.45 (s, 2 H) | MS obsd. (ESI$^+$) [(M + H)$^+$] 462 |
| 7 | $^1$H NMR (400 MHz, CD$_3$OD) δ ppm 8.22 (d, J = 5.05 Hz, 1 H), 8.05 (s, 1 H), 8.02 (d, J = 1.77 Hz, 2 H), 7.75 (d, J = 1.77 Hz, 1 H), 7.46 (d, J = 8.34 Hz, 2 H), 7.31 (dd, J = 8.59, 1.77 Hz, 1 H), 7.14 (d, J = 8.59 Hz, 1 H), 7.06 (d, J = 4.80 Hz, 1 H), 5.41 (s, 2 H), 1.76-1.69 (m, 2 H), 1.58-1.66 (m, 2 H) | MS obsd. (ESI$^+$) [(M + H)$^+$] 444 |
| 8 | $^1$H NMR (400 MHz, CD$_3$OD) δ ppm 8.30-8.22 (m, 1 H), 8.20-8.11 (m, 1 H), 7.85-7.67 (m, 3 H), 7.38-7.27 (m, 2 H), 7.27-7.18 (m, 1 H), 7.16-7.09 (m, 1 H), 6.63-6.48 (m, 2 H), 1.88-1.70 (m, 4 H) | MS obsd. (ESI$^+$) [(M + H)$^+$] 418 |

TABLE 2-continued

NMR and MS data of particular compounds

| Example No. | $^1$H NMR data | MW data |
|---|---|---|
| 9-1 | $^1$H NMR (400 MHz, CD$_3$OD) δ ppm 8.15-8.10 (m, 1 H), 7.99-7.93 (m, 2 H), 7.63-7.58 (m, 2 H), 7.54-7.49 (m, 1 H), 7.49-7.45 (m, 1 H), 7.45-7.42 (m, 1 H), 7.11-7.06 (m, 1 H), 7.01-6.96 (m, 1 H), 5.40 (s, 2 H), 3.19 (s, 3 H), 1.80-1.70 (m, 4 H) | MS obsd. (ESI$^+$) [(M + H)$^+$] 478 |
| 9-2 | $^1$H NMR (400 MHz, CD$_3$OD) δ ppm 8.16-8.08 (m, 2 H), 7.98-7.84 (m, 2 H), 7.75-7.64 (m, 1 H), 7.57-7.50 (m, 1 H), 7.50-7.36 (m, 2 H), 7.16-7.04 (m, 1 H), 7.04-6.96 (m, 1 H), 5.44-5.31 (m, 2 H), 3.18 (s, 3 H), 1.79-1.67 (m, 4 H) | MS obsd. (ESI$^+$) [(M + H)$^+$] 478 |

More particular compounds of formula I include the following:

5-{5-Chloro-2-[(2'-oxospiro[cyclopropane-1,3'-pyrrolo[2,3-c]pyridin]-1'(2'H)-yl)methyl]-1H-benzimidazol-1-yl}pyridine-2-carbonitrile;

Ethyl 4-{5-chloro-2-[(2'-oxospiro[cyclopropane-1,3'-pyrrolo[2,3-c]pyridin]-1'(2'H)-yl)methyl]-1H-benzimidazol-1-yl}benzoate;

1'-({5-Chloro-1-[6-(methylsulfonyl)pyridin-3-yl]-1H-benzimidazol-2-yl}methyl)spiro[cyclopropane-1,3'-pyrrolo[2,3-c]pyridin]-2'(1'H)-one;

1'-({5-chloro-1-[3-(methylsulfonyl)phenyl]-1H-benzimidazol-2-yl}methyl)spiro[cyclopropane-1,3'-pyrrolo[2,3-c]pyridin]-2'(1'H)-one;

1'-({5-chloro-1-[4-(methylsulfonyl)phenyl]-1H-benzimidazol-2-yl}methyl)spiro[cyclopropane-1,3'-pyrrolo[2,3-c]pyridin]-2'(1'H)-one;

3-{5-Chloro-2-[(2'-oxospiro[cyclopropane-1,3'-pyrrolo[2,3-c]pyridin]-1'(2'H)-yl)methyl]-1H-benzimidazol-1-yl}benzonitrile;

1'-{[5-Chloro-1-(6-methoxypyridin-3-yl)-1H-benzimidazol-2-yl]methyl}spiro[cyclopropane-1,3'-pyrrolo[2,3-c]pyridin]-2'(1'H)-one;

1'-({5-Chloro-1-[5-(methylsulfonyl)pyridin-3-yl]-1H-benzimidazol-2-yl}methyl)spiro[cyclopropane-1,3'-pyrrolo[2,3-c]pyridin]-2'(1'H)-one;

1'-({5-Chloro-1-[6-(methylsulfonyl)pyridin-2-yl]-1H-benzimidazol-2-yl}methyl)spiro[cyclopropane-1,3'-pyrrolo[2,3-c]pyridin]-2'(1'H)-one;

4-{5-Chloro-2-[(2'-oxospiro[cyclopropane-1,3'-pyrrolo[2,3-c]pyridin]-1'(2'H)-yl)methyl]-1H-benzimidazol-1-yl}benzoic acid;

4-{5-Chloro-2-[(6'-fluoro-2'-oxospiro[cyclopropane-1,3'-indol]-1'(2'H)-yl)methyl]-1H-benzimidazol-1-yl}benzoic acid; and 1'-{[5-Chloro-1-(6-hydroxypyridin-3-yl)-1H-benzimidazol-2-yl]methyl}spiro[cyclopropane-1,3'-pyrrolo[2,3-c]pyridin]-2'(1'H)-one.

Synthesis

The compounds of the present invention can be prepared by any conventional means. Suitable processes for synthesizing these compounds as well as their starting materials are provided in the schemes below and in the examples. All substituents, in particular, R$^1$ to R$^{10}$, W and X are as defined above unless otherwise indicated. Furthermore, and unless explicitly otherwise stated, all reactions, reaction conditions, abbreviations and symbols have the meanings well known to a person of ordinary skill in organic chemistry.

General Synthetic Route for Compound Ia (Scheme 1)

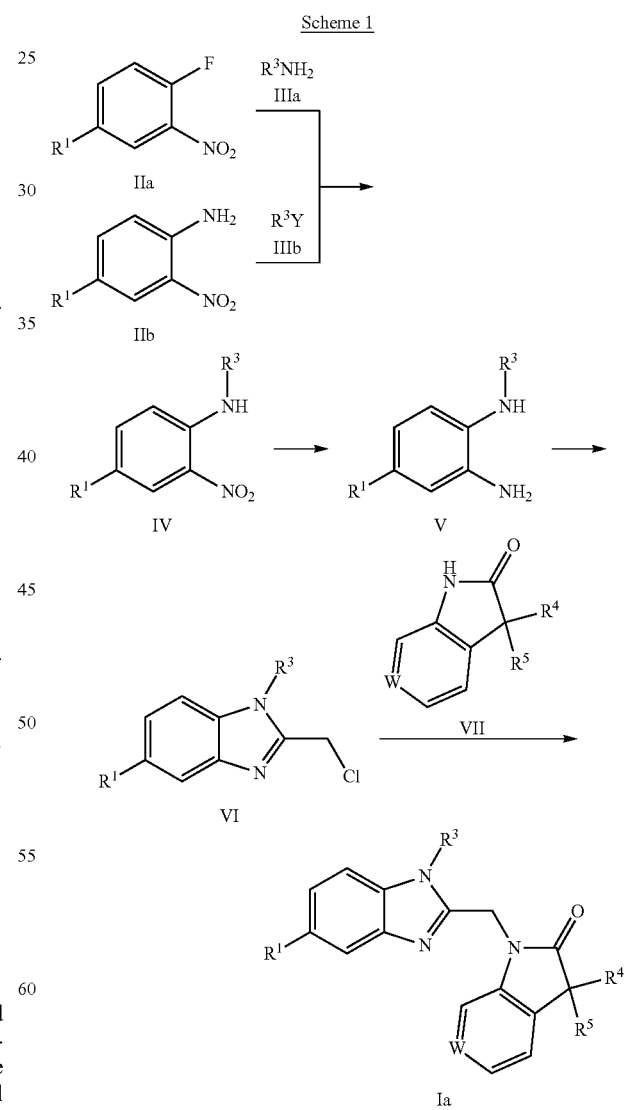

Y is Br, I or C$_{1-6}$alkylsulfonyl.

Compound Ia can be prepared according to Scheme 1.

o-Nitro-N-substituted aniline IV can be generated by reaction of fluorobenzene IIa with amine IIIa. The reaction can be carried out in the presence of a suitable base such as potassium 2-methylpropan-2-olate, sodium 2-methylpropan-2-olate, potassium carbonate or ethyl-diisopropylamine in a suitable organic solvent such as N,N-dimethylformamide at a temperature between 20° C. and 120° C. for several hours.

o-Nitro-N-substituted aniline IV can also be generated by reaction of aniline IIb with IIIb. The reaction can be carried out in the presence of a suitable base such as potassium carbonate in a suitable organic solvent such as N,N-dimethylformamide at a temperature between 100° C. and 160° C. under microwave irradiation for 30 minutes to several hours. The reaction can also be carried out with tris(dibenzylideneacetone)dipalladium, 4,5-bis(diphenylphosphino)-9,9-dimethylxanthene, and cesium carbonate in 1,4-dioxane at a temperature between 100° C. and 150° C. for several hours.

Diamine V can be prepared by reduction of nitro group of o-nitro-N-substituted aniline IVa. The reaction can be carried out in the presence of Raney nickel with hydrazine hydrate in an organic solvent such as methanol or ethanol at a temperature between room temperature and 80° C. for 10 minutes to several hours. The reaction can also be carried out in the presence of Raney nickel under hydrogen atmosphere at room temperature overnight.

2-(Chloromethyl)benzimidazole VI can be prepared by reaction of diamine V with bromoacetic acid. The reaction can be carried out in an aqueous solution of hydrochloric acid at a concentration between 4 N and 12 N at a temperature between 100° C. and 150° C. for several hours to several days. 2-(Chloromethyl)benzimidazole VI can also be prepared by reaction of diamine V with 2-chloro-1,1,1-trimethoxyethane or 2-chloro-1,1,1-triethoxyethane. The reaction can be carried out by heating diamine V with 2-chloro-1,1,1-trimethoxyethane or 2-chloro-1,1,1-triethoxyethane in the presence or absence of 4-methylbenzenesulfonic acid with or without ethanol at a temperature between 50° C. and 80° C. for several hours. Alternatively, the reaction can be carried out by heating diamine V with 2-chloro-1,1,1-trimethoxyethane or 2-chloro-1,1,1-triethoxyethane with or without ethanol at a temperature between 100° C. and 120° C. for one to several hours under microwave irradiation.

Compound Ia can be prepared by reaction of 2-(chloromethyl)benzimidazole VI with amide VII. The reaction can be carried out in the presence of a suitable base such as cesium carbonate, sodium hydride or potassium tert-butoxide in an organic solvent such as acetonitrile or N,N-dimethylformamide at a temperature between 0° C. and 100° C. for one to several hours.

General Synthetic Route for Compound Ib (Scheme 2)

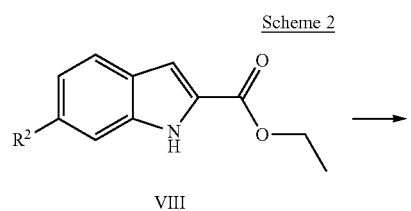

Scheme 2

VIII

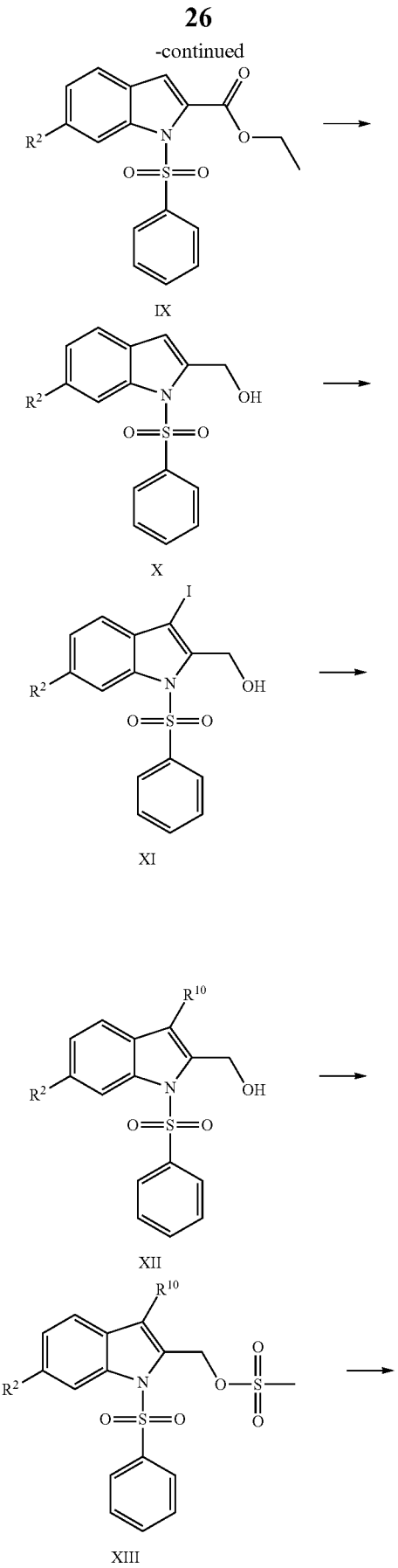

IX

X

XI

XII

XIII

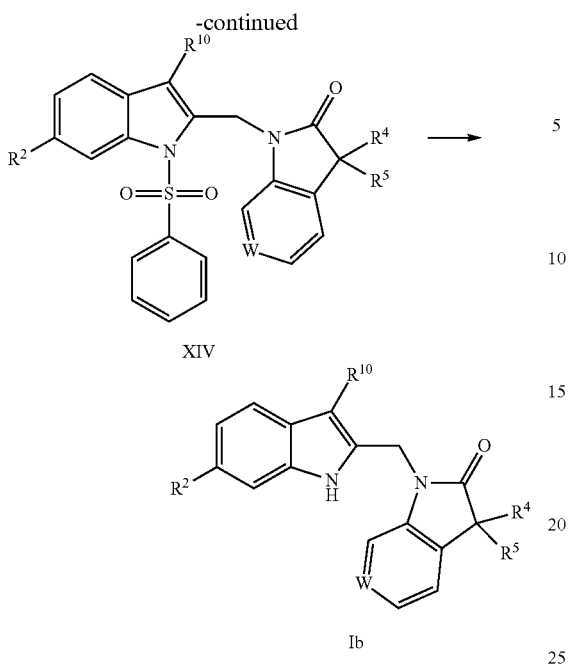

XIV

Ib

Compound Ib can be prepared according to Scheme 2.

N-protected indole IX can be prepared by reaction of indole VIII with benzenesulfonyl chloride. The reaction can be carried out in the presence of sodium hydride in N,N-dimethylformamide at a temperature between 0° C. and room temperature for one to several hours.

Hydroxy X can be prepared by reduction of ethyl ester IX. The reaction can be carried out by treating alkyl ester IX with lithium aluminum hydride in tetrahydrofuran at a temperature between 0° C. and room temperature for several hours.

3-Iodo-indole XI can be prepared by treating 2-hydroxymethyl-indole X with 1-iodopyrrolidine-2,5-dione. The reaction can be carried out in a suitable solvent such as acetonitrile at 0° C. for one to several hours.

3-Phenyl indole XII can be prepared by reaction of iodo XI with phenylboromic acid. The reaction can be carried out in the presence of a suitable palladium catalyst such as 1,1'-bis(diphenylphosphino)ferrocene-palladium(II)dichloride and a suitable base such as potassium carbonate in N,N-dimethylacetamide at a temperature between 50° C. and 100° C. for several hours.

Methanesulfonate XIII can be prepared by reaction of hydroxy XII with methanesulfonyl chloride. The reaction can be carried out by treating hydroxy XII with methanesulfonyl chloride with a suitable organic base such as triethylamine or diisopropylethylamine in dichloromethane at a temperature between 0° C. and room temperature for one to several hours.

Intermediate XIV can be prepared by reaction of methanesulfonate XIII with amide VII. The reaction can be carried out in the presence of a base such as cesium carbonate, sodium hydride or sodium tert-butoxide in an organic solvent such as acetonitrile or N,N-dimethylformamide at a temperature between 0° C. and room temperature for one to several hours.

Compound Ib can be prepared by cleavage of benzenesulfonyl group of XIV. The reaction can be carried out by treating XIV with tetra-n-butylammonium fluoride in a suitable solvent such as dichloromethane or tetrahydrofuran at room temperature for 30 minutes to several hours.

This invention also relates to a process for the preparation of a compound of formula I comprising the reaction of
(a) a Compound of Formula (A)

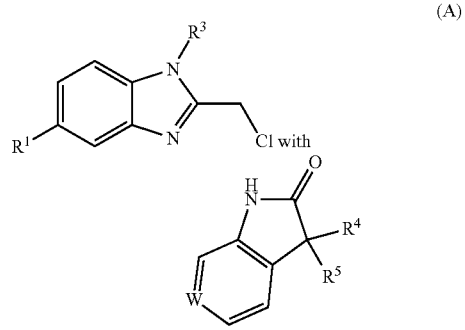

(A)

in the presence of a base;
(b) a Compound of Formula (B)

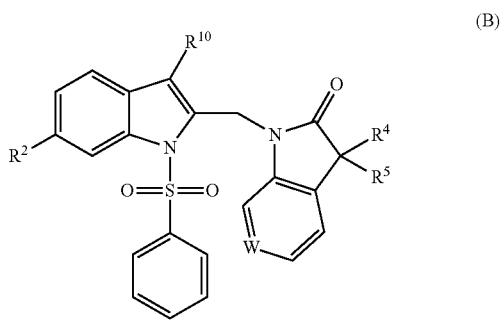

(B)

with tetra-n-butylammonium fluoride;
wherein $R^1$ to $R^5$, $R^{10}$, W and X are defined above unless otherwise indicated.

In step (a), the base can be for example cesium carbonate, sodium hydride or potassium tert-butoxide.

A compound of formula I when manufactured according to the above process is also an object of the invention.

Pharmaceutical Compositions and Administration

The invention also relates to a compound of formula I for use as therapeutically active sub stance.

Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compounds of formula (I) are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit RSV fusion protein. For example, such amount may be below the amount that is toxic to normal cells, or the mammal as a whole.

In one example, the pharmaceutically effective amount of the compound of the invention administered parenterally per dose will be in the range of about 0.1 to about 50 mg/kg, alternatively about 0.1 to about 20 mg/kg of patient body weight per day, with the typical initial range of compound used being about 0.3 to about 15 mg/kg/day. In another embodiment, oral unit dosage forms, such as tablets and capsules, preferably contain from about 25 to about 100 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 25 mg to about 500 mg of the compound of the invention compounded with about 90 to about 30 mg anhydrous lactose, about 5 to about 40 mg sodium croscarmellose, about 5 to about 30 mg polyvinylpyrrolidone (PVP) K30, and about 1 to about 10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5 mg to 400 mg), of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a compound of Formula I, or a stereoisomer or pharmaceutically acceptable salt thereof. In a further embodiment includes a pharmaceutical composition comprising a compound of Formula I, or a stereoisomer or pharmaceutically acceptable salt thereof, together with a pharmaceutically acceptable carrier or excipient.

Indications and Methods of Treatment

The compounds of the invention can be utilized to inhibit RSV fusion protein, therefore prevent the virus cell syncytial function. Accordingly, the compounds of the invention are useful for the treatment or prophylaxis of RSV infection.

The invention relates to the use of a compound of formula I for the treatment or prophylaxis of respiratory syncytial virus infection.

The use of a compound of formula I for the preparation of medicaments useful in the treatment or prophylaxis diseases that are related to RSV infection is an object of the invention.

The invention relates in particular to the use of a compound of formula I for the preparation of a medicament for the treatment or prophylaxis of RSV infection.

Another embodiment includes a method of treating or preventing RSV infection in a mammal in need of such treatment, wherein the method comprises administering to said mammal a therapeutically effective amount of a compound of Formula I, a stereoisomer, tautomer, prodrug or pharmaceutically acceptable salt thereof.

Combination Therapy

The compounds of the invention can be used in combination with other antiviral ingredients for the treatment or prophylaxis of RSV infection.

EXAMPLES

The invention will be more fully understood by reference to the following examples. They should not, however, be construed as limiting the scope of the invention.

Abbreviations used herein are as follows:

μL: microliter
μm: micrometer
μM: micromoles per liter
AUC: area under the curve
$CD_3OD$: deuterated methanol
$CDCl_3$: deuterated chloroform
DMSO-$d_6$: deuterated dimethylsulfoxide
$EC_{50}$: the concentration of a compound where 50% of its maximal protection effect against viral induced CPE is observed
g: gram
HPLC: high performance liquid chromatography
Hz: Hertz
ICR: imprinting control region
J: coupling constants
LC/MS: Liquid chromatography/mass spectrometry
LongStrain: an A subtype RSV strain obtained from ATCC with catalog number VR-26
mg: milligram
MHz: megahertz
mL: milliliter
mm: millimeter
mmol: millimole MS (ESI): mass spectroscopy (electron spray ionization)
NMR: nuclear magnetic resonance
obsd.: observed
Ph: phenyl
PK: Pharmacokinetics
SDPK: single dose pharmacokinetics
Prep HPLC: preparative high performance liquid chromatography
TEA: triethylamine
TLC: thin layer chromatography
δ: chemical shift
ppm: parts per million General Experimental Conditions Intermediates and final compounds were purified by flash chromatography using one of the following instruments: i) Biotage SP1 system and the Quad 12/25 Cartridge module. ii) ISCO combi-flash chromatography instrument. Silica gel Brand and pore size: i) KP-SIL 60 Å, particle size: 40-60 μM; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using X Bridge™ Perp C$_{18}$ (5 μm, OBD™ 30×100 mm) column or SunFire™ Perp C$_{18}$ (5 μm, OBD™ 30×100 mm) column.

LC/MS spectra were obtained using a MicroMass Plateform LC (Waters™ alliance 2795-ZQ2000). Standard LC/MS conditions were as follows (running time 6 minutes):

Acidic condition: A: 0.1% formic acid in H$_2$O; B: 0.1% formic acid in acetonitrile;

Basic condition: A: 0.01% NH$_3$.H$_2$O in H$_2$O; B: acetonitrile;

Neutral condition: A: H$_2$O; B: acetonitrile.

Mass spectra (MS): generally only ions which indicate the parent mass are reported, and unless otherwise stated the mass ion quoted is the positive mass ion (M+H)$^+$.

The microwave assisted reactions were carried out in a Biotage Initiator Sixty.

NMR Spectra were obtained using Bruker Avance 400 MHz.

All reactions involving air-sensitive reagents were performed under an argon atmosphere. Reagents were used as received from commercial suppliers without further purification unless otherwise noted.

The following examples were prepared by the general methods outlined in the schemes above. They are intended to illustrate the meaning of the present invention but should by no means represent a limitation within the meaning of the present invention.

PREPARATIVE EXAMPLES

Example 1

5-{5-Chloro-2-[(2'-oxospiro[cyclopropane-1,3'-pyrrolo[2,3-c]pyridin]-1'(2'H)-yl)methyl]-1H-benzimidazol-1-yl}pyridine-2-carbonitrile Step 1: Preparation of 5-nitropyridine-2-carbonitrile

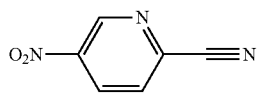 [SMILES: N#Cc1ccc([N+](=O)[O-])cn1]

A mixture of 2-bromo-5-nitropyridine (12.0 g, 59.1 mmol, CAS No.: 4487-59-6) and copper (I) cyanide (7.94 g, 88.7 mmol) in N,N-dimethylformamide (50 mL) was heated under reflux for 16 hours. After being cooled down to room temperature, the reaction mixture was poured into water and then extracted with ethyl acetate (100 mL×3). The combined organic layer was washed with brine, and then dried over sodium sulfate and filtered. The filtrate was concentrated in vacuo to afford 8.0 g of 5-nitropyridine-2-carbonitrile (yield was 90.8%).

Step 2: Preparation of 5-aminopyridine-2-carbonitrile

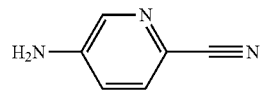

To a solution of 5-nitropyridine-2-carbonitrile (7.0 g, 46.9 mmol) in methanol (150 mL) was added 10% palladium on carbon (2.0 g) and carbamic acid (7.0 g, 115 mmol). After being heated under reflux for 16 hours, the resulting mixture was filtered and the filtrate was concentrated in vacuo. The residue was dissolved in water (150 mL) and the resulting mixture was extracted with ethyl acetate (150 mL×3). The organic layer was dried over sodium sulfate and concentrated in vacuo to afford 5.1 g of 5-aminopyridine-2-carbonitrile (yield was 91.3%).

Step 3: Preparation of 5-[(4-chloro-2-nitrophenyl)amino]pyridine-2-carbonitrile

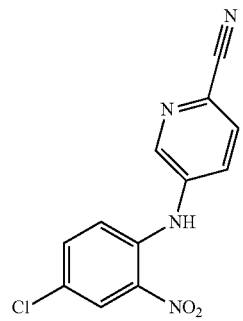 [SMILES: N#Cc1ccc(Nc2ccc(Cl)cc2[N+](=O)[O-])cn1]

A mixture of 4-chloro-1-fluoro-2-nitrobenzene (880 mg, 5.03 mmol, CAS No.: 345-18-6), 5-aminopyridine-2-carbonitrile (1.19 g, 10.0 mmol, CAS No.: 55338-73-3) and potassium 2-methylpropan-2-olate (1.12 g, 10.0 mmol) in N,N-dimethylformamide (20 mL) was stirred at room temperature overnight. The reaction mixture was poured into ice-water. The precipitate was collected by filtration to afford 0.7 g of 5-[(4-chloro-2-nitrophenyl)amino]pyridine-2-carbonitrile (yield was 50.7%).

Step 4: Preparation of 5-[(2-amino-4-chlorophenyl) amino]pyridine-2-carbonitrile

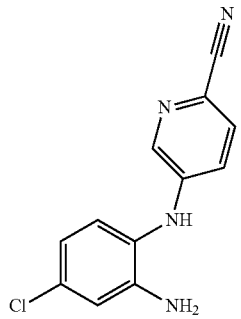 [SMILES: N#Cc1ccc(Nc2ccc(Cl)cc2N)cn1]

To a solution of 5-[(4-chloro-2-nitrophenyl)amino]pyridine-2-carbonitrile (600 mg, 2.18 mmol) in methanol (10 mL) was added Raney nickel (200 mg) under nitrogen protection. The resulting mixture was stirred under hydrogen atmosphere at room temperature overnight. The resulting mixture was filtered through a pad of silica gel. The filtrate was concentrated in vacuo. The residue was purified by preparative TLC (50% ethyl acetate in petroleum ether) to afford 190 mg of 5-[(2-amino-4-chlorophenyl)amino] pyridine-2-carbonitrile (yield was 35.6%).

Step 5: Preparation of 5-[5-chloro-2-(chloromethyl)-1H-benzimidazol-1-yl]pyridine-2-carbonitrile

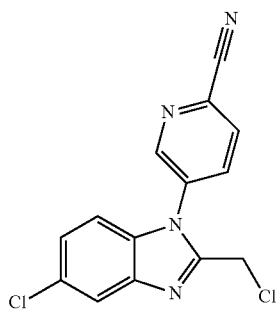 [SMILES: N#Cc1ccc(-n2c(CCl)nc3cc(Cl)ccc32)cn1]

A mixture of 5-[(2-amino-4-chlorophenyl)amino]pyridine-2-carbonitrile (190 mg, 0.78 mmol) and 2-chloro-1,1,1-trimethoxyethane (602 mg, 3.89 mmol, CAS No.: 74974-54-2) in ethanol (10 mL) was heated under reflux for 2 hours. The resulting reaction mixture was concentrated in vacuo and the residue was purified by preparative TLC (50% ethyl acetate in petroleum ether) to afford 200 mg of 5-[5-chloro-2-(chloromethyl)-1H-benzimidazol-1-yl]pyridine-2-carbonitrile (yield was 84.6%).

Step 6: Preparation of dimethyl 2-(3-nitro-4-pyridyl)propanedioate

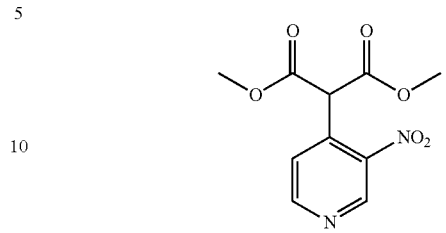

To a cooled suspension of sodium hydride (22.5 g, 0.56 mol) in dry toluene (1500 mL) was added dimethyl malonate (92 g, 0.7 mol) dropwise while stirring at a temperature between 0° C. and 10° C. under $N_2$. After the addition, the mixture was stirred for 30 minutes. Then to the resulting mixture was added a solution of 4-chloro-3-nitro-pyridine (75.0 g, 0.47 mmol, CAS No: 13091-23-1) in dry toluene (1000 mL) dropwise at room temperature and then the resulting mixture was heated under reflux overnight. After the completion of the reaction, the reaction mixture was cooled to room temperature and then poured into ice-water and then extracted with EtOAc (500 mL×3). The combined organic layer was dried over sodium sulphate and then concentrated in vacuo. The residue was purified by flash chromatography to afford 55 g of dimethyl 2-(3-nitro-4-pyridyl)propanedioate (yield was 38.6%).

Step 7: Preparation of methyl 2-(3-nitro-4-pyridyl)acetate

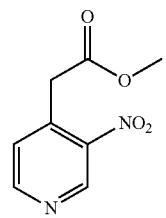

A mixture of dimethyl 2-(3-nitro-4-pyridyl)propanedioate (5.1 g, 20 mmol), lithium chloride (1.59 g, 37.6 mmol), water (0.36 g, 20 mmol) and dimethyl sulfoxide (100 mL) was heated at 100° C. for 8 hours. The reaction mixture was cooled, and then diluted with ethyl acetate (150 mL) and then washed successively with water (100 mL) and brine (100 mL). The combined aqueous layers were extracted with ethyl acetate (100 mL×2). The organic layer was combined, and then dried over sodium sulphate, then filtered and concentrated in vacuo. The residue was purified by flash chromatography to give 2.4 g of methyl 2-(3-nitro-4-pyridyl)acetate (yield was 61.2%).

Step 8: Preparation of methyl 2-(3-nitro-4-pyridyl)prop-2-enoate

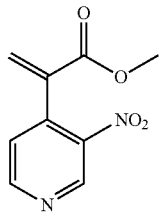

A mixture of methyl 2-(3-nitro-4-pyridyl)acetate (37 g, 0.189 mol), benzyl(triethyl)ammonium chloride (86 g, 1.233 mol) and potassium carbonate (53 g, 0.378 mol) in dry toluene (1500 mL) was degassed and then paraformaldehyde (37 g, 1.233 mol) was added in portions to the mixture. The reaction mixture was heated with stirring at 80° C. for 1 hour. The resulting mixture was cooled to room temperature and then the solvent was removed. The residue was dissolved in ice-water (1000 mL), and then extracted with ethyl acetate (500 mL×2). The combined organic layer was washed with brine (500 mL), and then dried over sodium sulphate and then concentrated in vacuo. The residue was purified by flash column to afford 21.6 g of methyl 2-(3-nitro-4-pyridyl)prop-2-enoate as a brown solid (yield was 55%).

Step 9: Preparation of methyl 1-(3-nitro-4-pyridyl)cyclopropanecarboxylate

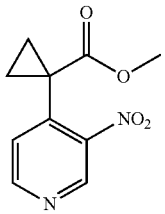 [SMILES: COC(=O)C1(c2ccncc2[N+](=O)[O-])CC1]

To a degassed solution of trimethyl sulfoxonium chloride (11.6 g, 0.072 mol, CAS No.: 47987-92-8) in dry tetrandrofuran (200 mL) was added potassium tert-butoxide (5.9 g, 0.072 mol) at 0° C. The resulting mixture was stirred at room temperature for 1 hour. Then to the resulting mixture was added dropwise a solution of methyl 2-(3-nitro-4-pyridyl)prop-2-enoate (10 g, 0.048 mol) in dry tetrandrofuran (200 mL). The reaction mixture was stirred at room temperature for 5 hours, and then poured into ice-water, then extracted with ethyl acetate (500 mL×2). The combined organic layer was washed with brine (500 mL), and then dried over sodium sulphate and then concentrated in vacuo. The residue was purified by flash column to afford 3.5 g of methyl 1-(3-nitro-4-pyridyl)cyclopropanecarboxylate as a brown solid (yield was 33%).

Step 10: Preparation of methyl 1-(3-amino-4-pyridyl)cyclopropanecarboxylate

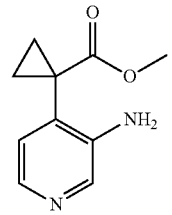

A solution of methyl 1-(3-nitro-4-pyridyl)cyclopropanecarboxylate (3.5 g, 15.7 mmol) in 200 mL of ethanol was stirred under hydrogen (50 psi) at room temperature for 6 hours in the presence of 10% palladium on carbon (350 mg). The resulting mixture was filtered and the filtrate was concentrated in vacuo to afford 2.9 g of methyl 1-(3-amino-4-pyridyl)cyclopropanecarboxylate (yield was 96%), which was used for the next step reaction without further purification.

Step 11: Preparation of spiro[cyclopropane-1,3'-pyrrolo[2,3-c]pyridin]-2'(1'H)-one

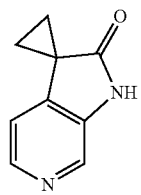 [SMILES: O=C1Nc2cnccc2C12CC2]

To a solution of methyl 1-(3-amino-4-pyridyl)cyclopropanecarboxylate (2.9 g, 15 mmol) in 100 mL of water was added tetrafluoroboric acid (6.6 mL, 50 wt % in water). The mixture was heated under reflux for 30 minutes and then cooled to room temperature. The mixture was then adjusted to pH 8 by addition of sodium bicarbonate. The reaction mixture was extracted with ethyl acetate (100 mL×5). The combined organic layer was dried over sodium sulphate and then concentrated in vacuo to afford 0.6 g of spiro[cyclopropane-1,3'-pyrrolo[2,3-c]pyridin]-2'(1'H)-one (yield was 25%).

Step 12: Preparation of 5-{5-chloro-2-[(2'-oxospiro[cyclopropane-1,3'-pyrrolo[2,3-c]pyridin]-1'(2'H)-yl)methyl]-1H-benzimidazol-1-yl}pyridine-2-carbonitrile A mixture of 5-[5-chloro-2-(chloromethyl)-1H-benzimidazol-1-yl]pyridine-2-carbonitrile (150 mg, 0.495 mmol), spiro[cyclopropane-1,3'-pyrrolo[2,3-c]pyridin]-2'(1'H)-one (87.0 mg, 0.544 mmol) and cesium carbonate (194 mg, 0.594 mmol) in acetonitrile (5 mL) was stirred at room temperature overnight. The resulting mixture was filtered and the filtrate was purified by preparative HPLC to afford 65 mg of the title product.

Example 2-1

1'-({5-Chloro-1-[2-(methylsulfonyl)pyridin-4-yl]-1H-benzimidazol-2-yl}methyl)spiro[cyclopropane-1,3'-pyrrolo[2,3-c]pyridin]-2'(1'H)-one

Step 1: Preparation of 2,4-bis(methylsulfonyl)pyridine

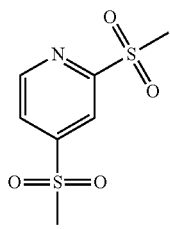

A mixture of 2,4-dichloropyridine (1.68 g, 11.0 mmol, CAS No.: 26452-80-2), sodium methanesulfinate (3.96 g, 33.0 mmol, 85% purity, CAS No.: 20277-69-4) and tetrabutylammonium chloride (917 mg, 3.3 mmol) in N,N-dimethylformamide (10 mL) was heated at 150° C. under microwave irradiation for 1 hour. The resulting mixture was then stirred with water (20 mL). The precipitate was collected by filtration to afford 1.59 g of 2,4-bis(methylsulfonyl)pyridine as a light pale solid (yield was 61.5%).

Step 2: Preparation of N-(4-chloro-2-nitrophenyl)-2-(methylsulfonyl)pyridin-4-amine

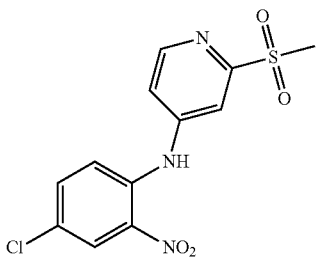

A mixture of 2,4-bis(methylsulfonyl)pyridine (1.41 g, 6.0 mmol), 4-chloro-2-nitroaniline (1.03 g, 6.0 mmol, CAS No.: 89-63-4) and potassium carbonate (828 mg, 6.0 mmol) in N,N-dimethylformamide (10 mL) was heated at 160° C. for 30 minutes under microwave irradiation. The resulting mixture was diluted with ethyl acetate (30 mL) and then washed with brine (20 mL). The organic layer was dried over sodium sulfate and then concentrated in vacuo. The residue was purified by flash chromatography on silica gel (eluting with 0-8% methanol in dichloromethane) to afford 864 mg of N-(4-chloro-2-nitrophenyl)-2-(methylsulfonyl)pyridin-4-amine as an orange solid (yield was 44.0%) and 294 mg of N-(4-chloro-2-nitrophenyl)-4-(methylsulfonyl)pyridin-2-amine (yield was 15.0%).

Step 3: Preparation of 4-chloro-N¹-[2-(methylsulfonyl)pyridin-4-yl]benzene-1,2-diamine

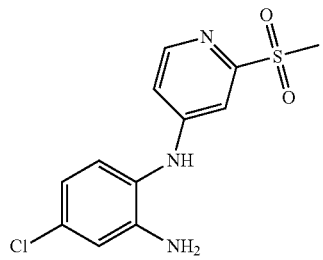 [SMILES: CS(=O)(=O)c1cc(Nc2ccc(Cl)cc2[N+](=O)[O-])ccn1]

A mixture of N-(4-chloro-2-nitrophenyl)-2-(methyl sulfonyl)pyridin-4-amine (839 mg, 2.57 mmol), Raney nickel (1.0 g of suspension in water) and hydrazine hydrate (1.5 mL, 85% aqueous solution) in ethanol (30 mL) was stirred at room temperature overnight. The resulting mixture was filtered and the filtrate was concentrated in vacuo. The residue was dissolved in dichloromethane (20 mL) and the solution was washed with brine (15 mL). The organic layer was dried over sodium sulfate and then concentrated in vacuo to afford 660 mg of 4-chloro-N¹-[2-(methylsulfonyl)pyridin-4-yl]benzene-1,2-diamine (yield was 86.5%).

Step 4: Preparation of 5-chloro-2-(chloromethyl)-1-[2-(methylsulfonyl)pyridin-4-yl]-1H-benzimidazole

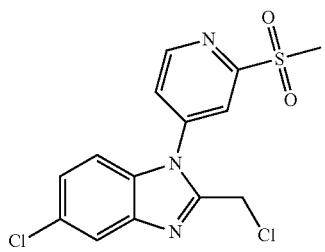 [SMILES: CS(=O)(=O)c1cc(-n2c(CCl)nc3cc(Cl)ccc32)ccn1]

A mixture of 4-chloro-N¹-[2-(methylsulfonyl)pyridin-4-yl]benzene-1,2-diamine (296 mg, 1.0 mmol) and 2-chloro-1,1,1-triethoxyethane (852 mg, 4.34 mmol) was heated at 120° C. for 2 hours under microwave irradiation. The resulting mixture was concentrated in vacuo and the residue was stirred with petroleum ether (40 mL). The precipitate was collected by filtration to afford 300 mg of 5-chloro-2-(chloromethyl)-1-[2-(methylsulfonyl)pyridin-4-yl]-1H-benzimidazole as a brown solid (yield was 84.3%).

Step 5: Preparation of 1'-({5-chloro-1-[2-(methylsulfonyl)pyridin-4-yl]-1H-benzimidazol-2-yl}methyl)spiro[cyclopropane-1,3'-pyrrolo[2,3-c]pyridin]-2'(1'H)-one A mixture 5-chloro-2-(chloromethyl)-1-[2-(methylsulfonyl)pyridin-4-yl]-1H-benzimidazole (150 mg, 0.42 mmol), spiro[cyclopropane-1,3'-pyrrolo[2,3-c]pyridin]-2'(1'H)-one (74 mg, 0.46 mmol) and cesium carbonate in acetonitrile (5 mL) was heated at 80° C. for 1 hour. The resulting mixture was concentrated in vacuo after filtration. The residue was purified by preparative HPLC to afford 120 mg of the title product as a light brown solid.

Example 2-2

1'-({5-Chloro-1-[4-(ethylsulfonyl)pyridin-2-yl]-1H-benzimidazol-2-yl}methyl)spiro[cyclopropane-1,3'-pyrrolo[2,3-c]pyridin]-2'(1'H)-one The title compound was prepared in analogy to Example 2-1 by using sodium ethanesulfinate (CAS No.:20035-59-4) instead of sodium methanesulfinate.

Example 3

Ethyl(4-{5-chloro-2-[(2'-oxospiro[cyclopropane-1,3'-pyrrolo[2,3-c]pyridin]-1'(2'H)-yl)methyl]-1H-benzimidazol-1-yl}phenyl)acetate

Step 1: Preparation of ethyl {4-[(4-chloro-2-nitrophenyl)amino]phenyl}acetate

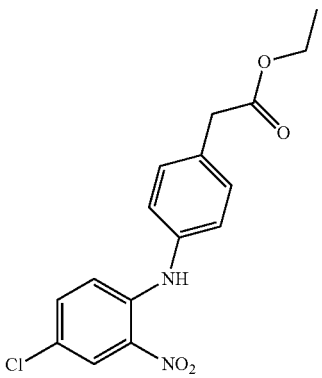 [SMILES: CCOC(=O)Cc1ccc(Nc2ccc(Cl)cc2[N+](=O)[O-])cc1]

A mixture of ethyl(4-aminophenyl)acetate (205 mg, 1.14 mmol, CAS No.: 5438-70-0), 4-chloro-1-fluoro-2-nitrobenzene (200 mg, 1.14 mmol) and ethyl-diisopropyl-amine (0.80 mL, 4.57 mmol) in N,N-dimethylformamide (5 mL) was heated at 100° C. for 12 hours. The resulting mixture was diluted with water (20 mL) and then extracted with ethyl acetate (25 mL×3). The combined organic layer was washed with brine (30 mL×2), and then dried over sodium sulfate and then concentrated in vacuo. The crude ethyl {4-[(4-chloro-2-nitrophenyl)amino]phenyl}acetate was used directly for the next step without further purification.

Step 2: Preparation of ethyl {4-[5-chloro-2-(chloromethyl)-1H-benzimidazol-1-yl]phenyl}acetate

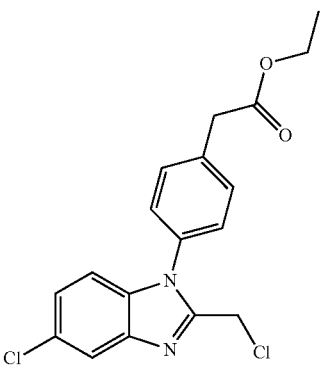 [SMILES: CCOC(=O)Cc1ccc(-n2c(CCl)nc3cc(Cl)ccc32)cc1]

Ethyl {4-[5-chloro-2-(chloromethyl)-1H-benzimidazol-1-yl]phenyl}acetate was prepared in analogy to 5-chloro-2-(chloromethyl)-1-[2-(methylsulfonyl)pyridin-4-yl]-1H-benzimidazole in Example 2-1 by using ethyl {4-[(4-chloro-2-nitrophenyl)amino]phenyl}acetate instead of N-(4-chloro-2-nitrophenyl)-2-(methylsulfonyl)pyridin-4-amine.

Step 3: Preparation of ethyl(4-{5-chloro-2-[(2'-oxospiro[cyclopropane-1,3'-pyrrolo[2,3-c]pyridin]-1'(2'H)-yl)methyl]-1H-benzimidazol-1-yl}phenyl)acetate To a solution of spiro[cyclopropane-1,3'-pyrrolo[2,3-c]pyridin]-2'(1'H)-one (88 mg, 0.55 mmol) in N,N-dimethylformamide (5 mL) was added sodium 2-methylpropan-2-olate (55 mg, 0.57 mmol). The mixture was stirred at room temperature for 30 minutes, then the reaction mixture was added to the solution of ethyl {4-[5-chloro-2-(chloromethyl)-1H-benzimidazol-1-yl]phenyl}acetate (200 mg, 0.55 mmol) in N,N-dimethylformamide (5 mL) dropwise. The mixture was stirred for 30 minutes and then neutralized to pH 7 by addition of 10% hydrochloric acid. The resulting mixture was purified by preparative HPLC to afford the title product.

Example 4-1

1'-[(5-Chloro-1-phenyl-1H-benzimidazol-2-yl)methyl]spiro[cyclopropane-1,3'-pyrrolo[2,3-c]pyridin]-2'(1'H)-one

Step 1: Preparation of 4-chloro-2-nitro-N-phenylaniline

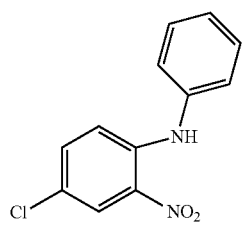 [SMILES: O=[N+]([O-])c1cc(Cl)ccc1Nc1ccccc1]

A sealed vial containing a mixture of 4-chloro-2-nitroaniline (1.72 g, 10.0 mmol), iodobenzene (2.04 g, 10.0 mmol, CAS No.: 591-50-4), tris(dibenzylideneacetone)dipalladium (183 mg, 0.20 mmol), 4,5-bis(diphenylphosphino)-9,9-dimethylxanthene (231 mg, 0.40 mmol), cesium carbonate (6.52 g, 20.0 mmol) and 1,4-dioxane (10 mL) was heated at 120° C. overnight after purged and backfilled with argon. The resulting mixture was concentrated in vacuo and the residue was purified by flash column (eluting with 0-50% of ethyl acetate in petroleum) to afford 1.89 g of 4-chloro-2-nitro-N-phenylaniline as brown viscous oil (yield was 75.6%).

Step 2: Preparation of 1'-[(5-chloro-1-phenyl-1H-benzimidazol-2-yl)methyl]spiro[cyclopropane-1,3'-pyrrolo[2,3-c]pyridin]-2'(1'H)-one The title compound was prepared in analogy to Example 2-1 by using 4-chloro-2-nitro-N-phenyl aniline instead of N-(4-chloro-2-nitrophenyl)-2-(methyl sulfonyl)pyridin-4-amine.

Example 4-2

Ethyl 4-{5-chloro-2-[(2'-oxospiro[cyclopropane-1,3'-pyrrolo[2,3-c]pyridin]-1'(2'H)-yl)methyl]-1H-benzimidazol-1-yl}benzoate The title compound was prepared in analogy to Example 4-1 by using ethyl 4-bromobenzoate (CAS No.: 5798-75-4) instead of iodobenzene.

Example 4-3

1'-({5-Chloro-1-[6-(methylsulfonyl)pyridin-3-yl]-1H-benzimidazol-2-yl}methyl)spiro[cyclopropane-1,3'-pyrrolo[2,3-c]pyridin]-2'(1'H)-one Step 1: Preparation of 5-bromo-2-(methylsulfonyl)pyridine

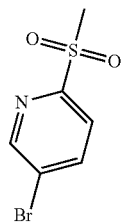

A mixture of 2-chloro-5-bromo-pyridine (9.80 g, 50.0 mmol, CAS No.: 53939-30-3) and sodium methanethiolate (5.25 g, 75.0 mmol, CAS No.: 5188-07-8) in N,N-dimethylformamide (25 mL) was stirred at room temperature for 3 hours. The reaction mixture was diluted with water (50 mL) and then extracted with ethyl acetate (60 mL×3). The combined organic layer was washed with brine (100 mL×2), and then dried over sodium sulfate and then concentrated in vacuo to afford a mixture of 5-bromo-2-(methylsulfanyl)pyridine and 2,5-bis(methylsulfanyl)pyridine, which was used directly for the next step.

To a cooled solution of the above mixture in dichloromethane (80 mL) was added 3-chlorobenzenecarboperoxoic acid (30.2 g, 175 mmol) in portions. The resulting mixture was stirred at room temperature for 2 days. The reaction mixture was then washed with 1N sodium hydroxide (50 mL×2) after filtration. The organic layer was dried over sodium sulfate and then concentrated in vacuo to afford 9.26 g of the crude 5-bromo-2-(methylsulfonyl)pyridine (yield was 78.4%), which was used for the next step directly without any purification.

Step 2: Preparation of 1'-({5-chloro-1-[6-(methylsulfonyl)pyridin-3-yl]-1H-benzimidazol-2-yl}methyl)spiro[cyclopropane-1,3'-pyrrolo[2,3-c]pyridin]-2'(1'H)-one The title compound was prepared in analogy to Example 4-1 by using 5-bromo-2-(methylsulfonyl)pyridine instead of iodobenzene.

Example 4-4

1'-({5-chloro-1-[3-(methylsulfonyl)phenyl]-1H-benzimidazol-2-yl}methyl)spiro[cyclopropane-1,3'-pyrrolo[2,3-c]pyridin]-2'(1'H)-one The title compound was prepared in analogy to Example 4-1 by using 1-bromo-3-(methylsulfonyl)benzene (CAS No.: 34896-80-5) instead of iodobenzene.

Example 4-5

1'-({5-Chloro-1-[4-(methylsulfonyl)phenyl]-1H-benzimidazol-2-yl}methyl)spiro[cyclopropane-1,3'-pyrrolo[2,3-c]pyridin]-2'(1'H)-one The title compound was prepared in analogy to Example 4-1 by using 1-bromo-4-(methylsulfonyl)benzene (CAS No.: 3466-32-8) instead of iodobenzene.

Example 4-6

Methyl 3-{5-chloro-2-[(2'-oxospiro[cyclopropane-1,3'-pyrrolo[2,3-c]pyridin]-1'(2'H)-yl)methyl]-1H-benzimidazol-1-yl}benzoate The title compound was prepared in analogy to Example 4-1 by using methyl 3-bromobenzoate (CAS No.: 618-89-3) instead of iodobenzene.

Example 4-7

3-{5-Chloro-2-[(2'-oxospiro[cyclopropane-1,3'-pyrrolo[2,3-c]pyridin]-1'(2'H)-yl)methyl]-1H-benzimidazol-1-yl}benzonitrile The title compound was prepared in analogy to Example 4-1 by using 4-chloro-1-fluoro-2-nitrobenzene and 3-bromobenzonitrile (CAS No.: 6952-59-6) instead of 4-chloro-2-nitroaniline and iodobenzene.

Example 4-8

1'-{[1-(3-Acetylphenyl)-5-chloro-1H-benzimidazol-2-yl]methyl}spiro[cyclopropane-1,3'-pyrrolo[2,3-c]pyridin]-2'(1'H)-one The title compound was prepared in analogy to Example 4-1 by using 4-chloro-1-fluoro-2-nitrobenzene and 1-(3-bromophenyl)ethanone (CAS No.: 2142-63-4) instead of 4-chloro-2-nitroaniline and iodobenzene.

Example 4-9

1'-{[5-Chloro-1-(6-methoxypyridin-3-yl)-1H-benzimidazol-2-yl]methyl}spiro[cyclopropane-1,3'-pyrrolo[2,3-c]pyridin]-2'(1'H)-one The title compound was prepared in analogy to Example 4-1 by using 4-chloro-1-fluoro-2-nitrobenzene and 5-bromo- 2-methoxypyridine (CAS No.: 13472-85-0) instead of 4-chloro-2-nitroaniline and iodobenzene.

Example 5-1

1'-({5-Chloro-1-[5-(methylsulfonyl)pyridin-3-yl]-1H-benzimidazol-2-yl}methyl)spiro[cyclopropane-1,3'-pyrrolo[2,3-c]pyridin]-2'(1'H)-one Step 1: Preparation of 5-bromo-N-(4-chloro-2-nitrophenyl)pyridin-3-amine

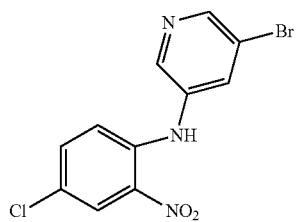 [SMILES: O=[N+]([O-])c1cc(Cl)ccc1Nc1cncc(Br)c1]

5-Bromo-N-(4-chloro-2-nitrophenyl)pyridin-3-amine was prepared in analogy to 4-chloro-2-nitro-N-phenylaniline in Example 4-1 by using 3-bromo-5-iodopyridine (CAS No.: 233770-01-9) instead of iodobenzene.

Step 2: Preparation of N-(4-chloro-2-nitrophenyl)-5-(methylsulfonyl)pyridin-3-amine

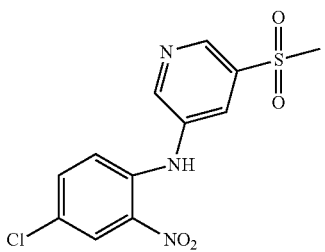 [SMILES: CS(=O)(=O)c1cncc(Nc2ccc(Cl)cc2[N+](=O)[O-])c1]

A mixture of 5-bromo-N-(4-chloro-2-nitrophenyl)pyridin-3-amine (326 mg, 1.0 mmol), sodium methanesulfinate (240 mg, 2.0 mmol, 85% purity, CAS No.: 20277-69-4), copper(I) iodide (38.1 mg, 0.10 mmol), L-pyrrolidine-2-carboxylic acid (23.2 mg, 0.20 mmol) and sodium hydroxide (8.0 mg, 0.20 mmol) in dimethyl sulfoxide (4.0 mL) and water (0.8 mL) was heated at 150° C. for 1 hour under microwave irradiation. The resulting mixture was diluted with water (10 mL) and then extracted with ethyl acetate (20 mL×2). The combined organic layer was washed with brine (20 mL), and then dried over sodium sulfate and then concentrated in vacuo. The residue was purified by flash column (eluting with 0-30% ethyl acetate in petroleum) to afford 156 mg of N-(4-chloro-2-nitrophenyl)-5-(methylsulfonyl)pyridin-3-amine as a brown solid (yield was 47.9%).

Step 3: Preparation of 1'-({5-chloro-1-[5-(methylsulfonyl)pyridin-3-yl]-1H-benzimidazol-2-yl}methyl)spiro[cyclopropane-1,3'-pyrrolo[2,3-c]pyridin]-2'(1'H)-one The title compound was prepared in analogy to Example 3-1 by using N-(4-chloro-2-nitrophenyl)-5-(methylsulfonyl)pyridin-3-amine instead of ethyl {4-[(4-chloro-2-nitrophenyl)amino]phenyl}acetate.

Example 5-2

1'-({5-Chloro-1-[6-(methylsulfonyl)pyridin-2-yl]-1H-benzimidazol-2-yl}methyl)spiro[cyclopropane-1,3'-pyrrolo[2,3-c]pyridin]-2'(1'H)-one The title compound was prepared in analogy to Example 5-1 by using 2,6-dibromopyridine (CAS No.: 626-05-1) instead of 3-bromo-5-iodopyridine.

Example 5-3

1'-({5-Chloro-1-[3-methyl-5-(methylsulfonyl)phenyl]-1H-benzimidazol-2-yl}methyl)spiro[cyclopropane-1,3'-pyrrolo[2,3-c]pyridin]-2'(1'H)-one The title compound was prepared in analogy to Example 5-1 by using 1,3-dibromo-5-methylbenzene (CAS No.: 615-59-8) instead of 3-bromo-5-iodopyridine.

Example 6-1

4-{5-Chloro-2-[(2'-oxospiro[cyclopropane-1,3'-pyrrolo[2,3-c]pyridin]-1'(2'H)-yl)methyl]-1H-benzimidazol-1-yl}benzoic acid A solution of ethyl 4-{5-chloro-2-[(2'-oxospiro[cyclopropane-1,3'-pyrrolo[2,3-c]pyridin]-1'(2'H)-yl)methyl]-1H-benzimidazol-1-yl}benzoate (200 mg, 0.42 mmol, Example 4-2) in tetrahydrofuran (4 mL) was stirred with 1M aqueous solution of lithium hydroxide (4 mL) at room temperature for 2 hours. The resulting mixture was concentrated in vacuo to remove the organic solvent, and then acidified with 1N hydrochloric acid to pH<7. The precipitate was collected by filtration and then dried in vacuo to afford 178 mg of the title product.

Example 6-2

3-{5-Chloro-2-[(2'-oxospiro[cyclopropane-1,3'-pyrrolo[2,3-c]pyridin]-1'(2'H)-yl)methyl]-1H-benzimidazol-1-yl}benzoic acid The title compound was prepared in analogy to Example 6-1 by using methyl 3-{5-chloro-2-[(2'-oxospiro[cyclopropane-1,3'-pyrrolo[2,3-c]pyridin]-1'(2'H)-yl)methyl]-1H-benzimidazol-1-yl}benzoate (Example 4-6) instead of ethyl 4-{5-chloro-2-[(2'-oxospiro[cyclopropane-1,3'-pyrrolo[2,3-c]pyridin]-1'(2'H)-yl)methyl]-1H-benzimidazol-1-yl}benzoate.

Example 6-3

4-{5-Chloro-2-[(6'-fluoro-2'-oxospiro[cyclopropane-1,3'-indol]-1'(2'H)-yl)methyl]-1H-benzimidazol-1-yl}benzoic acid Step 1: Preparation of ethyl 4-{5-chloro-2-[(6'-fluoro-2'-oxospiro[cyclopropane-1,3'-indol]-1'(2'H)-yl)methyl]-1H-benzimidazol-1-yl}benzoate

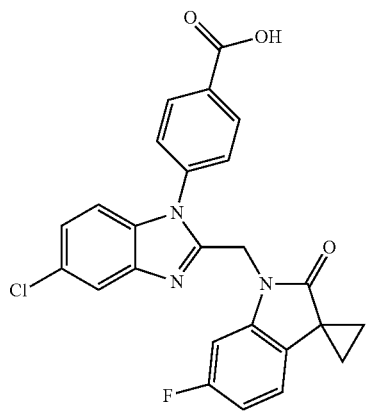 [SMILES: O=C(O)c1ccc(-n2c(CN3C(=O)C4(CC4)c4ccc(F)cc43)nc3cc(Cl)ccc32)cc1]

Ethyl 4-{5-chloro-2-[(6'-fluoro-2'-oxospiro[cyclopropane-1,3'-indol]-1'(2'H)-yl)methyl]-1H-benzimidazol-1-yl}benzoate was prepared in analogy to Example 4-1 by using ethyl 4-aminobenzoate instead of iodobenzene.

Step 2: Preparation of 4-{5-chloro-2-[(6'-fluoro-2'-oxospiro[cyclopropane-1,3'-indol]-1'(2'H)-yl)methyl]-1H-benzimidazol-1-yl}benzoic acid The title compound was prepared in analogy to Example 6-1 by using ethyl 4-{5-chloro-2-[(6'-fluoro-2'-oxospiro[cyclopropane-1,3'-indol]-1'(2'H)-yl)methyl]-1H-benzimidazol-1-yl}benzoate instead of ethyl 4-{5-chloro-2-[(2'-oxospiro[cyclopropane-1,3'-pyrrolo[2,3-c]pyridin]-1'(2'H)-yl)methyl]-1H-benzimidazol-1-yl}benzoate.

Example 7

4-{5-Chloro-2-[(2'-oxospiro[cyclopropane-1,3'-pyrrolo[2,3-c]pyridin]-1'(2'H)-yl)methyl]-1H-benzimidazol-1-yl}benzamide A mixture of ethyl 4-{5-chloro-2-[(2'-oxospiro[cyclopropane-1,3'-pyrrolo[2,3-c]pyridin]-1'(2'H)-yl)methyl]-1H-benzimidazol-1-yl}benzoate (95 mg, 0.20 mmol, Example 4-2) and 7 N ammonia solution in methanol was heated at 90° C. for 4 hours under microwave irradiation. The resulting mixture was concentrated in vacuo. The residue was purified by preparative HPLC to afford 4.0 mg of the title product.

Example 8

1'-{[5-Chloro-1-(6-hydroxypyridin-3-yl)-1H-benzimidazol-2-yl]methyl}spiro[cyclopropane-1,3'-pyrrolo[2,3-c]pyridin]-2'(1'H)-one A mixture of 1'-{[5-chloro-1-(6-methoxypyridin-3-yl)-1H-benzimidazol-2-yl]methyl}spiro[cyclopropane-1,3'-pyrrolo[2,3-c]pyridin]-2'(1'H)-one (Example 4-9) and boron tribromide (CAS No.: 5967-37-3) in dichloromethane was heated under reflux for 2 hours. The resulting mixture was concentrated in vacuo and the residue was purified by preparative HPLC to afford the title product.

Example 9-1

1'-({6-Chloro-3-[4-(methylsulfonyl)phenyl]-1H-indol-2-yl}methyl)spiro[cyclopropane-1,3'-pyrrolo[2,3-c]pyridin]-2'(1'H)-one Step 1: Preparation of methyl 5-chloro-1-(phenylsulfonyl)-1H-indole-2-carboxylate

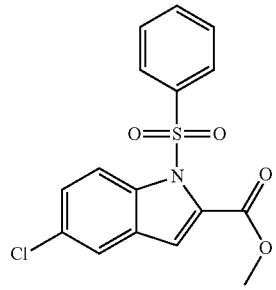 [SMILES: COC(=O)c1cc2cc(Cl)ccc2n1S(=O)(=O)c1ccccc1]

To a suspension of methyl 5-chloro-1H-indole-2-carboxylate (7.56 g, 36.0 mmol, CAS No.: 10517-21-2) and sodium hydride (1.70 g, 43.0 mmol, 60% purity in mineral oil) in N,N-dimethylformamide (100 mL) was added benzenesulfonyl chloride (6.1 mL, 47.0 mmol, CAS No.: 98-09-9) dropwise in an ice-water bath. After being stirred at room temperature for 2 hours, the mixture was then poured into ice-water (100 mL). The resulting precipitate was collected by filtration, which was washed with petroleum ether (50 mL), and then dried in vacuo to afford 11.6 g of methyl 5-chloro-1-(phenylsulfonyl)-1H-indole-2-carboxylate as a pale white solid (yield was 92%).

Step 2: Preparation of [5-chloro-1-(phenylsulfonyl)-1H-indol-2-yl]methanol

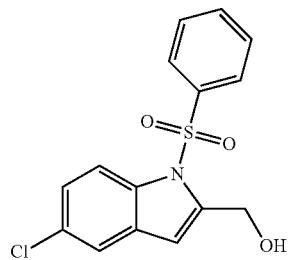 [SMILES: O=S(=O)(c1ccccc1)n1c(CO)cc2cc(Cl)ccc21]

To a suspension of lithium aluminium hydride (1.9 g, 50 mmol) in tetrahydrofuran (150 mL) at 0° C. was added methyl 5-chloro-1-(phenylsulfonyl)-1H-indole-2-carboxylate (11.6 g, 33 mmol) in portions. After being stirred at room temperature for 3 hours, the resulting mixture was quenched with methanol, then filtered through a celite pad.

The filtrate was concentrated in vacuo to afford 9.7 g of [5-chloro-1-(phenylsulfonyl)-1H-indol-2-yl]methanol as brown oil (yield was 91%).

Step 3: Preparation of [6-chloro-3-iodo-1-(phenyl-sulfonyl)-1H-indol-2-yl]methanol

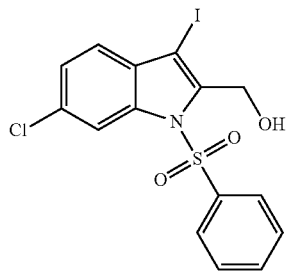 [SMILES: O=S(=O)(c1ccccc1)n1c(CO)c(I)c2ccc(Cl)cc21]

To a cooled solution of [5-chloro-1-(phenylsulfonyl)-1H-indol-2-yl]methanol (642 mg, 2.00 mmol) in acetonitrile (25 mL) was added 1-iodopyrrolidine-2,5-dione (450 mg, 2.0 mmol, CAS No.: 516-12-1) slowly at 0° C. The resulting mixture was stirred at 0° C. for 1 hour and then concentrated in vacuo. The residue was purified by flash column to afford [6-chloro-3-iodo-1-(phenylsulfonyl)-1H-indol-2-yl]methanol.

Step 4: Preparation of {6-chloro-3-[4-(methylsulfonyl)phenyl]-1-(phenylsulfonyl)-1H-indol-2-yl}methanol

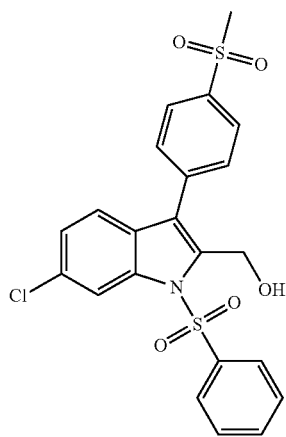 [SMILES: CS(=O)(=O)c1ccc(-c2c(CO)n(S(=O)(=O)c3ccccc3)c3cc(Cl)ccc23)cc1]

A mixture of [6-chloro-3-iodo-1-(phenylsulfonyl)-1H-indol-2-yl]methanol (447 mg, 1.0 mmol), 4-methanesulfonylphenylboronic acid (200 mg, 1.0 mmol, CAS No.: 149104-88-1), 1,1'-bis(diphenylphosphino)ferrocene-palladium(II) dichloride (41.0 mg, 0.05 mmol) and potassium carbonate (276 mg, 2.0 mmol) in N,N-dimethylacetamide (4 mL) was heated at 80° C. under nitrogen atmosphere for 2 hours. The resulting mixture was diluted with water (50 mL) and then extracted with ethyl acetate (100 mL). The organic layer was dried over sodium sulfate and then concentrated in vacuo. The residue was purified by flash column (eluting with 2% methanol in dichloromethane) to afford 381 mg of {6-chloro-3-[4-(methylsulfonyl)phenyl]-1-(phenylsulfonyl)-1H-indol-2-yl}methanol (yield was 80.0%).

Step 5: Preparation of 1'-({6-chloro-3-[4-(methylsulfonyl)phenyl]-1H-indol-2-yl}methyl)spiro[cyclopropane-1,3'-pyrrolo[2,3-c]pyridin]-2'(1'H)-one To a cooled solution of {6-chloro-3-[4-(methylsulfonyl)phenyl]-1-(phenylsulfonyl)-1H-indol-2-yl}methanol (380 mg, 0.80 mmol) in dichloromethane (5 mL) was added methanesulfonyl chloride (100 mg, 0.88 mmol) and triethylamine (162 mg, 1.60 mmol) at 0° C. After being stirred at for 1 hour, the resulting mixture was diluted with dichloromethane (3 mL), and then washed with water and brine. The organic layer was dried over sodium sulfate and then concentrated in vacuo. The residue was dissolved in N,N-dimethylformamide (5 mL), sodium 2-methylpropan-2-olate (77 mg, 0.80 mmol) was added to the solution and then followed by the addition of spiro[cyclopropane-1,3'-pyrrolo[2,3-c]pyridin]-2'(1'H)-one) (128 mg, 0.80 mmol). After being stirred at room temperature overnight, the resulting mixture was extracted with ethyl acetate (100 mL). The organic layer was washed with water and brine, and then dried over sodium sulfate and then concentrated in vacuo. The residue was dissolved in dichloromethane (6 mL) and treated with tetra-n-butylammonium fluoride (2 mL, 1M in tetrahydrofuran). After being stirred at room temperature for 30 minutes, the mixture was concentrated in vacuo and the residue was purified by preparative HPLC to afford the title product.

Example 9-2

1'-({6-Chloro-3-[3-(methylsulfonyl)phenyl]-1H-indol-2-yl}methyl)spiro[cyclopropane-1,3'-pyrrolo[2,3-c]pyridin]-2'(1'H)-one The title compound was prepared in analogy to Example 8-1 by using 3-methanesulfonylphenylboronic acid (CAS No.: 373384-18-0) instead of 4-methanesulfonylphenylboronic acid.

BIOLOGICAL EXAMPLES

Example 40 Viral Cytopathic Effect (CPE) Assay

To measure anti-RSV activity of compounds, 96-well plates are seeded with $6 \times 10^3$ cells per well in Dulbecco's modified Eagle's medium (DMEM) containing 10% fetal bovine serum (FBS). Cells are infected the next day with sufficient RSV Long strain (ATCC) to produce an approximately 80-90% cytopathic effect after 6 days, in the presence of serial half-log diluted compound in a total volume of 200 µL per well. The viability of cells is assessed after 6 days using Cell Counting kit-8 (Dojindo Molecular Technologies). The absorbance at 450 nm and referenced at 630 nm is measured to determine 50% effective concentration ($EC_{50}$).

The compounds of the present invention were tested for their anti-RSV activity, and the activation as described herein. The Examples were tested in the above assay and found to have $EC_{50}$ of about 0.0001 µM to about 10 µM. Particular compound of formula (I) were found to have $EC_{50}$ of about 0.0001 µM to about 1 µM. Further particular compound of formula (I) were found to have $EC_{50}$ of about 0.0001 µM to about 0.1 µM.

Results of CPE assays are given in Table 1.

Example A

A compound of formula I can be used in a manner known per se as the active ingredient for the production of tablets of the following composition:

|  | Per tablet |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula I can be used in a manner known per se as the active ingredient for the production of capsules of the following composition:

|  | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

The invention claimed is:

1. Compounds of formula (I)

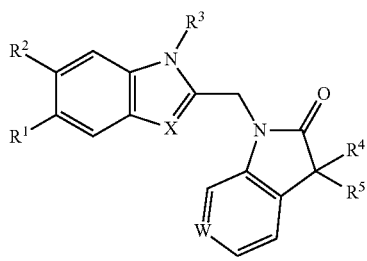

(I)

wherein
W is nitrogen or —$CR^9$, wherein $R^9$ is halogen;
X is nitrogen or —$CR^{10}$, provided that
when X is —$CR^{10}$, $R^1$ is hydrogen, $R^2$ is halogen, $R^3$ is hydrogen, wherein $R^{10}$ is $C_{1-6}$alkylsulfonylphenyl;
when X is nitrogen, $R^1$ is halogen, $R^2$ is hydrogen, $R^3$ is

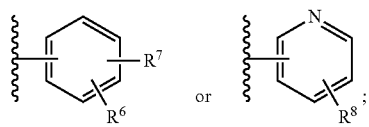

$R^4$ and $R^5$, with the carbon atom to which they are attached, form cycloalkyl;
$R^6$ is hydrogen or $C_{1-6}$alkyl;
$R^7$ is hydrogen, aminocarbonyl, $C_{1-6}$ alkoxycarbonyl-$C_yH_{2y}$—, $C_{1-6}$ alkylcarbonyl, $C_{1-6}$ alkylsulfonyl, carboxy or cyano, wherein y is 0-6;
$R^8$ is $C_{1-6}$alkylsulfonyl, $C_{1-6}$alkoxy, cyano or hydroxy;
or pharmaceutically acceptable salts thereof.

2. A compound according to claim 1, wherein
W is nitrogen or —CF;
X is nitrogen or —$CR^{10}$, provided that
when X is —$CR^{10}$, $R^1$ is hydrogen, $R^2$ is chloro, $R^3$ is hydrogen, wherein $R^{10}$ is methyl sulfonylphenyl;
when X is nitrogen, $R^1$ is chloro, $R^2$ is hydrogen, $R^3$ is or

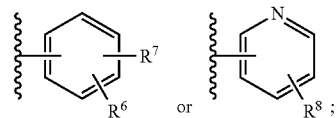

$R^4$ and $R^5$, with the carbon atom to which they are attached, form cyclopropyl;
$R^6$ is hydrogen or methyl;
$R^7$ is hydrogen, aminocarbonyl, ethoxycarbonyl, methoxycarbonyl, ethoxycarbonylmethyl, methylcarbonyl, methyl sulfonyl, carboxy or cyano;
$R^8$ is methoxy, methylsulfonyl, ethylsulfonyl, cyano or hydroxy;
or pharmaceutically acceptable salts thereof.

3. A compound according to claim 1 or a pharmaceutically acceptable salt thereof, wherein
$R^1$ is halogen;
$R^2$ is hydrogen;
$R^3$ is

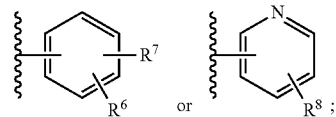

$R^4$ and $R^5$, with the carbon atom to which they are attached, form cycloalkyl;
$R^6$ is hydrogen or $C_{1-6}$alkyl;
$R^7$ is hydrogen, aminocarbonyl, $C_{1-6}$ alkoxycarbonyl-$C_yH_{2y}$—, $C_{1-6}$ alkylcarbonyl, $C_{1-6}$ alkylsulfonyl, carboxy or cyano, wherein y is 0-6;
$R^8$ is $C_{1-6}$alkylsulfonyl, $C_{1-6}$alkoxy, cyano or hydroxy;
W is nitrogen;
X is nitrogen.

4. A compound according to claim 1 or a pharmaceutically acceptable salt thereof, wherein
$R^1$ is chloro;
$R^2$ is hydrogen;
$R^3$ is

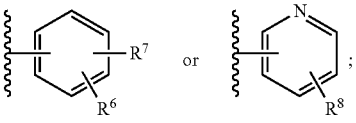

$R^4$ and $R^5$, with the carbon atom to which they are attached, form cyclopropyl;
$R^6$ is hydrogen or methyl;
$R^7$ is hydrogen, aminocarbonyl, ethoxycarbonyl, methoxycarbonyl, ethoxycarbonylmethyl, methylcarbonyl, methyl sulfonyl, carboxy or cyano;
$R^8$ is methoxy, methylsulfonyl, ethylsulfonyl, cyano or hydroxy;
W is nitrogen;
X is nitrogen.

5. A compound according to claim 1 or a pharmaceutically acceptable salt thereof, wherein
$R^1$ is hydrogen;
$R^2$ is halogen;
$R^3$ is hydrogen;
$R^4$ and $R^5$, with the carbon atom to which they are attached, form cycloalkyl;
W is nitrogen;
X is —$CR^{10}$, wherein $R^{10}$ is $C_{1-6}$alkylsulfonylphenyl.

6. A compound according to claim 1 or a pharmaceutically acceptable salt thereof, wherein
$R^1$ is halogen;
$R^2$ is hydrogen;
$R^3$ is carboxyphenyl;
$R^4$ and $R^5$, with the carbon atom to which they are attached, form cycloalkyl;
W is —$CR^9$, wherein $R^9$ is halogen;
X is nitrogen.

7. A compound according to claim 1 or a pharmaceutically acceptable salt thereof, wherein said compound is selected from:
  5-{5-Chloro-2-[(2'-oxospiro[cyclopropane-1,3'-pyrrolo[2,3-c]pyridin]-1'(2¹H)-yl)methyl]-1H-benzimidazol-1-yl}pyridine-2-carbonitrile;
  1'-({5-Chloro-1-[2-(methylsulfonyl)pyridin-4-yl]-1H-benzimidazol-2-yl}methyl)spiro[cyclopropane-1,3'-pyrrolo[2,3-c]pyridin]-2'(1'H)-one;
  1'-({5-Chloro-1-[4-(ethyl sulfonyl)pyridin-2-yl]-1H-benzimidazol-2-yl}methyl)spiro[cyclopropane-1,3'-pyrrolo[2,3-c]pyridin]-2'(1'H)-one;
  Ethyl (4-{5-chloro-2-[(2'-oxospiro[cyclopropane-1,3'-pyrrolo[2,3-c]pyridin]-1'(2'H)-yl)methyl]-1H-benzimidazol-1-yl}phenyl)acetate;
  1'-[(5-Chloro-1-phenyl-1H-benzimidazol-2-yl)methyl] spiro[cyclopropane-1,3'-pyrrolo[2,3-c]pyridin]-2'(1'H)-one;
  Ethyl 4-{5-chloro-2-[(2'-oxospiro[cyclopropane-1,3'-pyrrolo[2,3-c]pyridin]-1'(2'H)-yl)methyl]-1H-benzimidazol-1-yl}benzoate;
  1'-({5-Chloro-1-[6-(methylsulfonyl)pyridin-3-yl]-1H-benzimidazol-2-yl}methyl)spiro[cyclopropane-1,3'-pyrrolo[2,3-c]pyridin]-2'(1'H)-one;
  1'-({5-chloro-1-[3-(methylsulfonyl)phenyl]-1H-benzimidazol-2-yl}methyl)spiro[cyclopropane-1,3'-pyrrolo[2,3-c]pyridin]-2'(1'H)-one;
  1'-({5-chloro-1-[4-(methylsulfonyl)phenyl]-1H-benzimidazol-2-yl}methyl)spiro[cyclopropane-1,3'-pyrrolo[2,3-c]pyridin]-2'(1'H)-one;
  Methyl 3-{5-chloro-2-[(2'-oxospiro[cyclopropane-1,3'-pyrrolo[2,3-c]pyridin]-1'(2'H)-yl)methyl]-1H-benzimidazol-1-yl}benzoate;
  3-{5-Chloro-2-[(2'-oxospiro[cyclopropane-1,3'-pyrrolo[2,3-c]pyridin]-1'(2'H)-yl)methyl]-1H-benzimidazol-1-yl}benzonitrile;
  1'-{[1-(3-Acetylphenyl)-5-chloro-1H-benzimidazol-2-yl]methyl}spiro[cyclopropane-1,3'-pyrrolo[2,3-c]pyridin]-2'(1'H)-one;
  1'-{5-Chloro-1-(6-methoxypyridin-3-yl)-1H-benzimidazol-2-yl}methyl spiro[cyclopropane-1,3'-pyrrolo[2,3-c]pyridin]-2'(1'H)-one;
  1'-({5-Chloro-1-[5-(methylsulfonyl)pyridin-3-yl]-1H-benzimidazol-2-yl}methyl)spiro[cyclopropane-1,3'-pyrrolo[2,3-c]pyridin]-2'(1'H)-one;
  1'-({5-Chloro-1-[6-(methylsulfonyl)pyridin-2-yl]-1H-benzimidazol-2-yl}methyl)spiro[cyclopropane-1,3'-pyrrolo[2,3-c]pyridin]-2'(1'H)-one;
  1'-({5-Chloro-1-[3-methyl-5-(methylsulfonyl)phenyl]-1H-benzimidazol-2-yl}methyl)spiro[cyclopropane-1,3'-pyrrolo[2,3-c]pyridin]-2'(1'H)-one;
  4-{5-Chloro-2-[(2'-oxospiro[cyclopropane-1,3'-pyrrolo[2,3-c]pyridin]-1'(2'H)-yl)methyl]-1H-benzimidazol-1-yl}benzoic acid;
  3-{5-Chloro-2-[(2'-oxospiro[cyclopropane-1,3'-pyrrolo[2,3-c]pyridin]-1'(2'H)-yl)methyl]-1H-benzimidazol-1-yl}benzoic acid;
  4-{5-Chloro-2-[(6'-fluoro-2'-oxospiro[cyclopropane-1,3'-indol]-1'(2'H)-yl)methyl]-1H-benzimidazol-1-yl}benzoic acid;
  4-{5-Chloro-2-[(6'-fluoro-2'-oxospiro[cyclopropane-1,3'-indol]-1'(2'H)-yl)methyl]-1H-benzimidazol-1-yl}benzoic acid;
  1'-{[5-Chloro-1-(6-hydroxypyridin-3-yl)-1H-benzimidazol-2-yl]methyl}spiro[cyclopropane-1,3'-pyrrolo[2,3-c]pyridin]-2'(1'H)-one;
  1'-({6-Chloro-3-[4-(methylsulfonyl)phenyl]-1H-indol-2-yl}methyl)spiro[cyclopropane-1,3'-pyrrolo[2,3-c]pyridin]-2'(1'H)-one; and
  1'-({6-Chloro-3-[3-(methylsulfonyl)phenyl]-1H-indol-2-yl}methyl)spiro[cyclopropane-1,3'-pyrrolo[2,3-c]pyridin]-2'(1'H)-one.

8. A pharmaceutical composition comprising a compound of claim 1 and a therapeutically inert carrier.

* * * * *